(12) United States Patent
Zhang

(10) Patent No.: US 11,014,933 B2
(45) Date of Patent: May 25, 2021

(54) NON-PEPTIDE OPIOID RECEPTOR MODULATORS

(71) Applicant: Virginia Commonwealth University, Richmond, VA (US)

(72) Inventor: Yan Zhang, Glen Allen, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 16/726,420

(22) Filed: Dec. 24, 2019

(65) Prior Publication Data

US 2020/0216458 A1 Jul. 9, 2020

Related U.S. Application Data

(63) Continuation-in-part of application No. PCT/US2019/046980, filed on Aug. 19, 2019.

(60) Provisional application No. 62/720,552, filed on Aug. 21, 2018.

(51) Int. Cl.
*C07D 489/08* (2006.01)

(52) U.S. Cl.
CPC .................. *C07D 489/08* (2013.01)

(58) Field of Classification Search
None
See application file for complete search history.

(56) References Cited

U.S. PATENT DOCUMENTS 8,772,308 B2 * 7/2014 Zhang ............... A61P 25/32
514/282
8,980,908 B2 * 3/2015 Zhang ............... G01N 33/53
514/282

OTHER PUBLICATIONS

Database Registry Chemical Abstracts Service, Columbus, Ohio, Accession No. RN 1236037-40-3, Entered STN: Aug. 12, 2010.*
Database Registry Chemical Abstracts Service, Columbus, Ohio, Accession No. RN 1236037-41-4, Entered STN: Aug. 12, 2010.*

* cited by examiner

*Primary Examiner* — Samantha L Shterengarts
(74) *Attorney, Agent, or Firm* — W&C IP

(57) ABSTRACT

Non-peptide MOR opioid receptor modulators are provided. The compounds exhibit predominantly central activity and are used to treat e.g. substance use disorders, and pain.

6 Claims, 10 Drawing Sheets

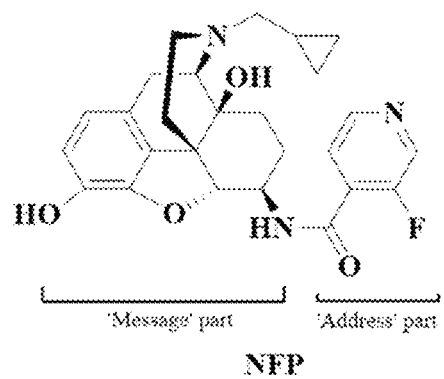
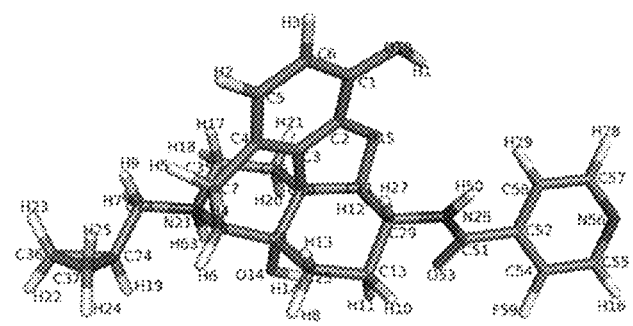
Figure 6A
Figure 6B
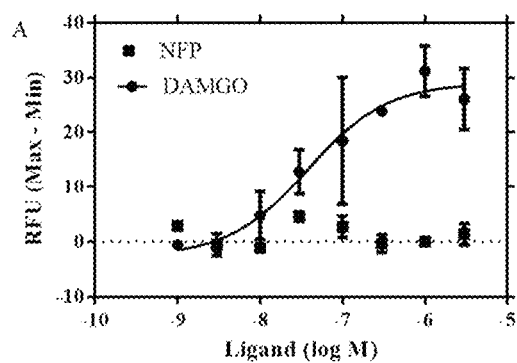
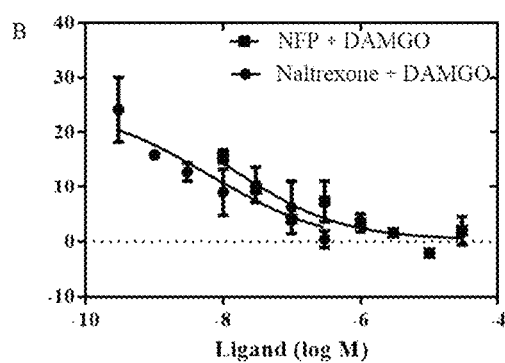
Figure 7A
Figure 7B

NON-PEPTIDE OPIOID RECEPTOR MODULATORS

CROSS REFERENCE TO RELATED APPLICATIONS

This application claims the benefit of U.S. Provisional Application No. 62/720,552, filed Aug. 21, 2018.

STATEMENT REGARDING FEDERALLY SPONSORED RESEARCH OR DEVELOPMENT

This invention was made with government support under Grant DA024022, Grant DA044855, and DA050311 awarded by the National Institutes of Health, Institute on Drug Abuse. The government has certain rights in the invention.

BACKGROUND OF THE INVENTION

Field of the Invention

This invention generally relates to non-peptide compounds that modulate opioid receptor activity. In particular, the compounds are modulators of the MOR opioid receptor with predominantly central activity and are used to treat e.g. substance use disorders and pain.

State of Technology

Opioid receptors belong to the class A Rhodopsin-like G-protein coupled receptor (GPCR) family and can be classified into four subtypes known as the µ opioid receptor (MOR), K opioid receptor (KOR), δ opioid receptor (DOR), and nociception opioid peptide (NOP) receptor. Among them, MOR is the main pharmacological target for opioid medications, such as morphine. Interaction between the MOR and $G\alpha_{i/o}$ leads to activation of the MOR which results in opening of inwardly rectifying $K^+$ (GIRK) channels, inhibition of the voltage-gated $Ca^{2+}$ (VGCC) channels and inhibition of adenylyl cyclase activity. These changes may further induce a variety of changes in membrane morphology, excite neurons, release neurotransmitters, and influence the expression of genes through the second messenger systems. The behavioral effects of MOR activation include beneficial antinociception and MOR agonists have been widely used for treating moderate to severe pain. However, numerous adverse effects have been associated with their use, including opioid-induced constipation (OIC), respiratory depression, and addiction. In fact, opioid addiction/abuse has become a global epidemic. It is reported that over 33,000 people died due to opioid overdose in the US alone in 2015, a more than 14-fold increase over the previous 20 years. Moreover, opioid abuse increases the prevalence of diseases such as HIV, tuberculosis, and hepatitis, especially for users who inject these drugs.

Currently, there are two approaches to treat opioid addiction: detoxification and maintenance therapy using opioid receptor agonists, partial agonists, and antagonists, including peptide opioids, such as CTOP and CTAP, (FIG. 10) and non-peptide opioids. These cyclic peptides are highly effective opioid antagonists with high MOR selectivity and metabolic stability, but poor bioavailability reduces their development as clinical therapeutics. Compared with peptide opioids, non-peptide opioid antagonists may have advantages of high bioavailability, easily crossing the blood-brain barrier (BBB), and good metabolic stability. The classical opioid antagonists used in opioid addiction treatments are naltrexone (NTX), used for long term treatment, and naloxone, used for short-acting treatment. While these opioid antagonists do not exhibit the side effects of opioid agonists, such as addiction and respiratory suppression, high doses of naltrexone and naloxone may induce hepatotoxicity and cardiovascular and pulmonary problems. In addition, the interactions between these compounds and the DOR or KOR may induce mood changes or block transmission of neurotransmitters.

Attempts to synthesize modulators that are highly selective for MOR, but which are not highly addictive and do not cause unwanted side effects, have met with varying degrees of success. There is still a pressing need in the art to provide better, more highly selective MOR modulators that are readily biologically available and which exhibit fewer side effects.

SUMMARY OF THE INVENTION

17-Cyclopropylmethyl-3,14β-dihydroxy-4,5α-epoxy-6β-[(4'-pyridyl)carboxamido]morphinan (NAP, FIG. 7), a 6β-N-4'-pyridyl substituted naltrexamine derivative, was previously identified as a peripheral MOR antagonist that may be used to treat OIC. Herein, the design, synthesis and biological evaluation of a new series of NAP derivatives is presented. Among these derivatives, N-((4R,4aS,7R,7aR,12bS)-3-(cyclopropylmethyl)-4a,9-dihydroxy-2,3,4,4a,5,6,7,7a-octahydro-1H-4,12-methanobenzofuro[3,2-e]isoquinolin-7-yl)-3-fluoroisonicotinamide (NFP) and 3-cyano-N-((4R,4aS,7R,7aR,12bS)-3-(cyclopropylmethyl)-4a,9-dihydroxy-2,3,4,4a,5,6,7,7a-octahydro-1H-4,12-methanobenzofuro[3,2-e]isoquinolin-7-yl)isonicotinamide (NYP) significantly antagonized the antinociception effect of morphine. Whereas NAP acted mainly peripherally, NFP and NYP advantageously act centrally. Furthermore, NFP produced significantly fewer withdrawal symptoms than naloxone at similar doses. Thus, these compounds can be used to treat opioid use disorders.

In an aspect of the invention, a compound of Formula I, or a pharmaceutically acceptable salt or solvate thereof, is provided:

Formula I

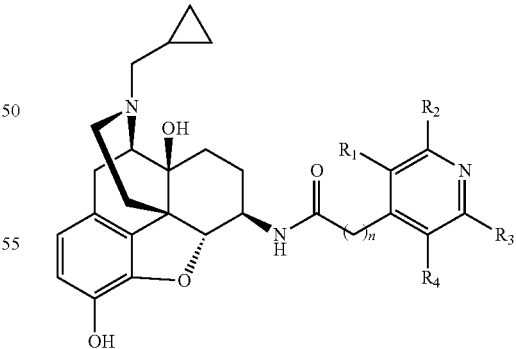

wherein, $R_1$, $R_2$, $R_3$ and $R_4$ are independently selected from the group consisting of: hydrogen; halogen; a substituted or unsubstituted $C_1$-$C_5$ alkyl; a 5-7 carbon ring that is saturated or unsaturated and may have one or more heteroatoms in the ring; a substituted or unsubstituted aryl or heteroaryl; an electron donating group; an electron withdrawing group; an alkoxycarbonyl; an acyl or a sulfonyl; and n is 0, 1, 2, or 3.

In some aspects, the compound is of Formula Ia:

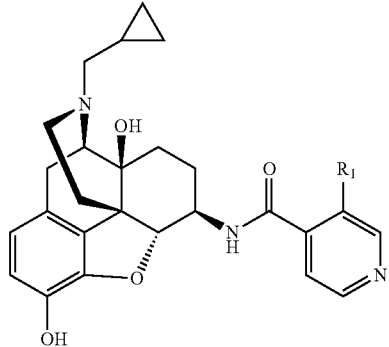

Formula Ia wherein $R_1$ is F, CN, $NO_2$, $CF_3$, COOH, $COOCH_3$, $C_2H_5$, isobutyl, cyclopentyl, cyclohexyl, cycloheptyl or phenyl.

In other aspects, the compound is of Formula Ib

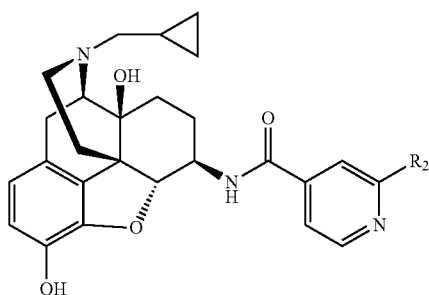

Formula Ib wherein $R_2$ is Cl, Br, CN, $CH_3$ or $OCH_3$.

Also provided is a method of preventing or treating opioid use disorders, alcoholism, pain, and/or a neurological disorder associated with opioid receptors in a subject in need thereof, comprising administering to the subject a therapeutically effective amount of i) a compound of Formula Ia:

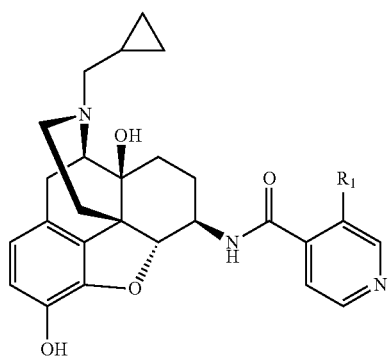

Formula Ia wherein, $R_1$ is F, CN, $NO_2$, $CF_3$, COOH, $COOCH_3$, $C_2H_5$, isobutyl, cyclopentyl, cyclohexyl, cycloheptyl or phenyl; or ii) a compound of Formula Ib:

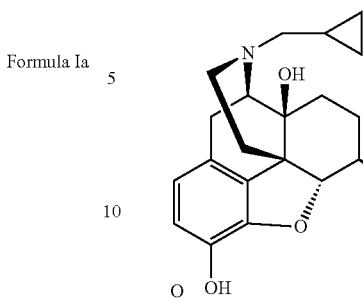

Formula Ib wherein R2 is Cl, Br, CN, $CH_3$ or $OCH_3$.

Also provided is a method of modulating a μ opioid receptor (MOR), comprising contacting the MOR with i) a compound of Formula Ia:

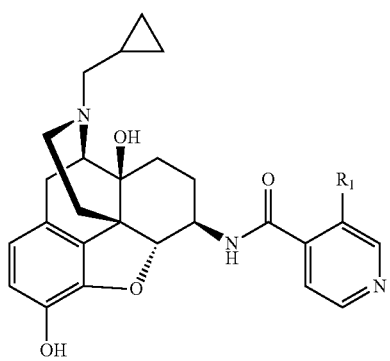

Formula Ia wherein $R_1$ is F, CN, $NO_2$, $CF_3$, COOH, $COOCH_3$, $C_2H_5$, isobutyl, cyclopentyl, cyclohexyl, cycloheptyl or phenyl; or ii) a compound of Formula Ib:

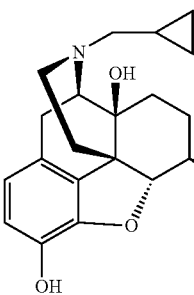

Formula Ib wherein R2 is Cl, Br, CN, $CH_3$ or $OCH_3$; wherein the step of contacting is performed under conditions that permit binding of the compound to the MOR and modulating the MOR. In some aspects, the step of contacting is performed in vivo in a subject or in vitro in a cultured cell. In further aspects, the cultured cell overexpresses the MOR.

In another aspect of the invention, the compound of Formula I is used to modulate opioid receptors.

In another aspect of the invention, the compound of Formula I is used to selectively modulate the MOR opioid receptor.

In another aspect, the compound of Formula I acts as a modulator to MOR and can be used for the treatment of opioid use disorders, alcoholism, pain, and neurological disorders associated with opioid receptors.

In another aspect, the compound of Formula I is NFP:

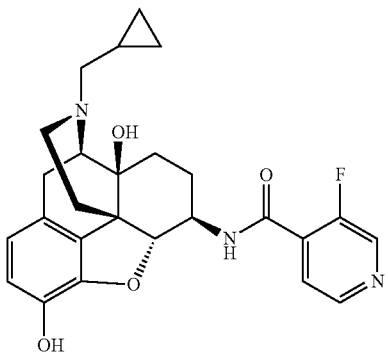

or a pharmaceutically acceptable salt or solvate thereof.

In another aspect, the compound of Formula I is NYP:

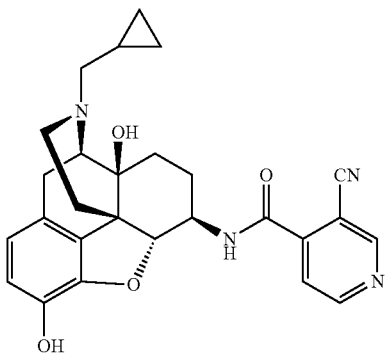

or a pharmaceutically acceptable salt or solvate thereof.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

FIGS. 6A and B. A, The chemical structure of NFP; B, atom notations from the docking studies.

FIGS. 7A and B. Calcium mobilization assay of NFP as an agonist (A) or an antagonist (B). The EC50 of DAMGO is 36.32±1.85 nM, $IC_{50}$ values of naltrexone and NFP are 6.62±1.45 nM and 76.09±2.50 nM, respectively. Data are presented as mean values±SEM (n=3).

DETAILED DESCRIPTION

Figure 10:
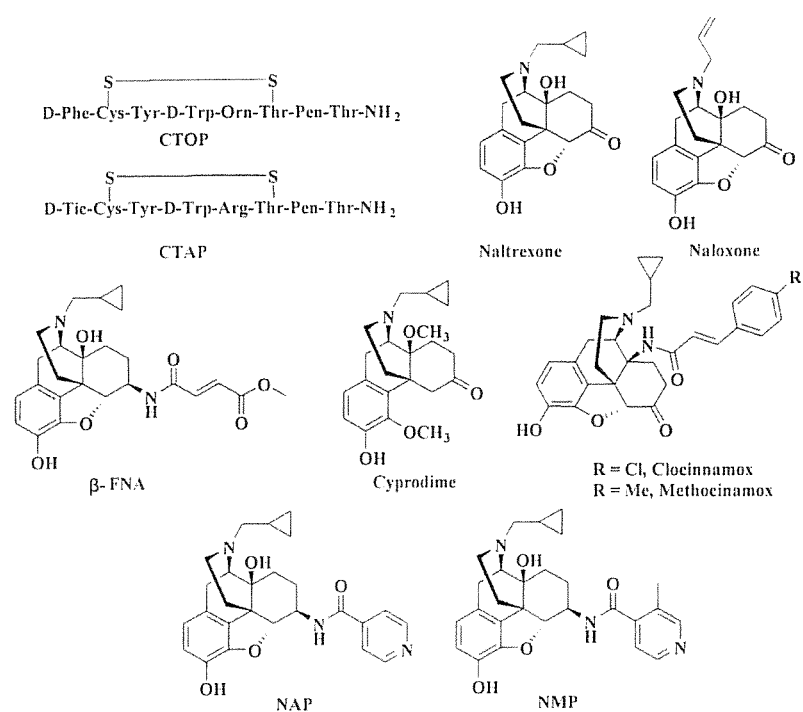
FIG. 10. Examples of MOR selective antagonists.

The influence on binding affinity of the 2' and 3' position on the pyridyl ring of NAP to opioid receptors was investigated. A series of new compounds were designed, synthesized, and biologically evaluated as third generation NAP derivatives. Two new compounds, NFP and NYP, were characterized in vitro and in vivo as opioid receptor modulators. Surprisingly, in contrast to peripherally acting NAP and N-((4R,4aS,7R,7aR,12bS)-3-(cyclopropylmethyl)-4a,9-dihydroxy-2,3,4,4a,5,6,7,7a-octahydro-1H-4,12-methano-benzofuro[3,2-e]isoquinolin-7-yl)-3-methylisonicotinamide (NMP); (see FIG. 10), these compounds were found to be centrally acting. In addition, they caused fewer withdrawal effects than naloxone. The compounds that were synthesized may find application in the treatment of opioid use disorders, as well as in the treatment of other neurological disorders implicating opioid receptors (e.g. alcoholism, pain, some psychiatric disorders, etc.).

As used herein, a "modulator" is a chemical compound that acts on a receptor e.g. as an antagonist or agonist or a partial agonist, etc. For example, an antagonist that binds the receptor may interfere with and/or inhibit its physiological activity. A partial agonist binds to and activates a receptor but has a lower efficacy than a full agonist.

The compounds provided herein, which include pharmaceutically acceptable salts and solvates, have a general formula as shown in Formula I:

Formula I

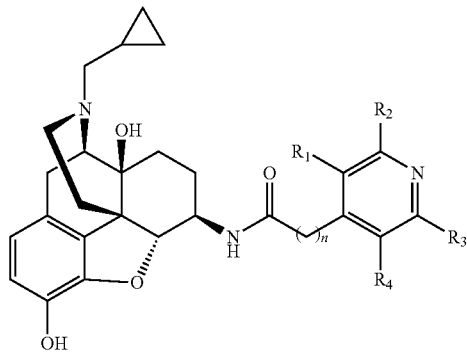

wherein, $R_1$, $R_2$, $R_3$ and $R_4$ are independently selected from the group consisting of: hydrogen; halogen (e.g. F, Cl, Br, I); a substituted or unsubstituted $C_1$-$C_5$ alkyl (e.g., a halogenated $C_1$-$C_5$ alkyl); a 5-7 carbon ring that is saturated or unsaturated and may have one or more heteroatoms in the ring; a substituted or unsubstituted aryl; an electron donating group (such as $C_1$-$C_5$ alkoxy, OH, etc.); an electron withdrawing group (such as $NO_2$, carboxyl, CN, $SO_2NH_2$, $SO_3H$, CHO, COR (where R is $C_1$-$C_5$ alkyl), $CO_2H$, aminocarbonyl ($CONH_2$), etc.); an alkoxycarbonyl; an acyl (e.g. OR where R is $C_1$-$C_5$ alkyl); a sulfonyl; etc.

In Formula 1, n can be 0, 1, 2, or 3.

In another aspect of the invention, what is provided is a compound of formula Ia, or a pharmaceutically acceptable salt, or solvate thereof:

Formula Ia

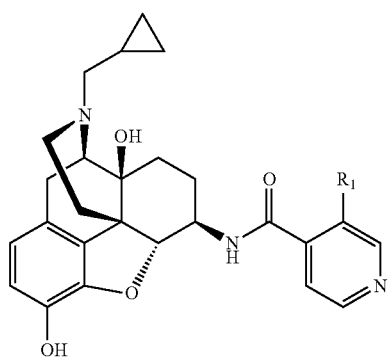

where, with respect to Formula I: n=0; R2, R3 and R4 are H; and $R_1$ is F, CN, $NO_2$, $CF_3$, COOH, $COOCH_3$, $C_2H_5$, isobutyl, cyclopentyl, cyclohexyl, cycloheptyl or phenyl.

In some embodiments, the compound of Formula Ia has any of these exemplary formulas:

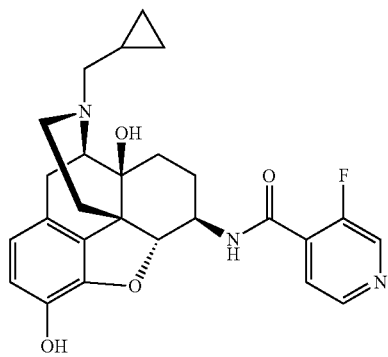

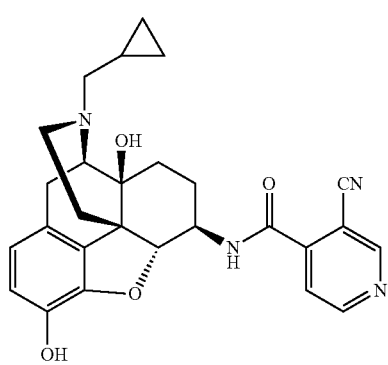

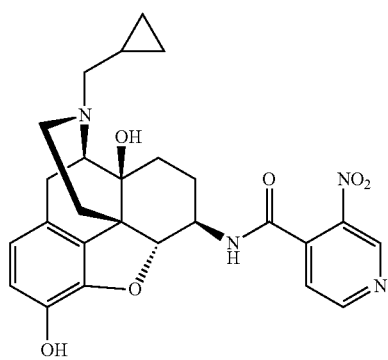

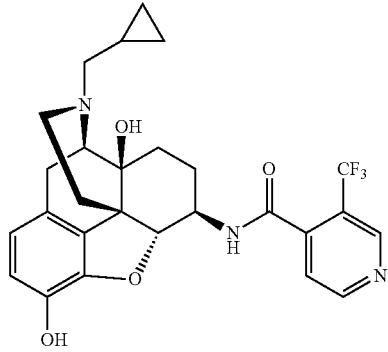

-continued
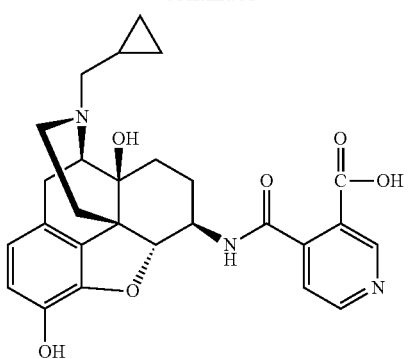
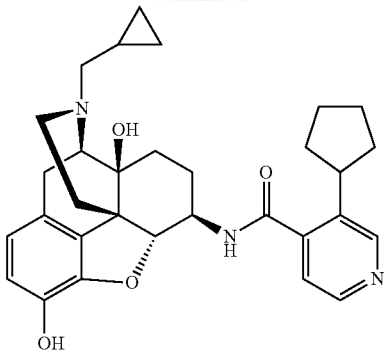
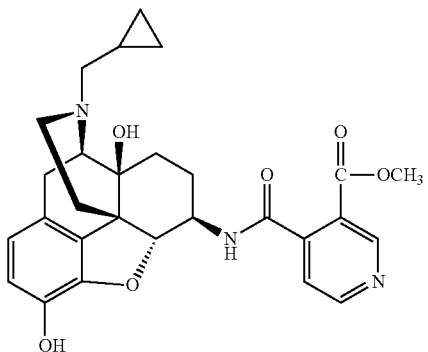
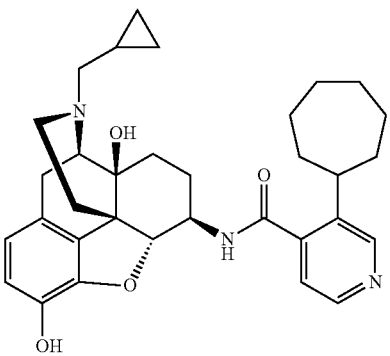
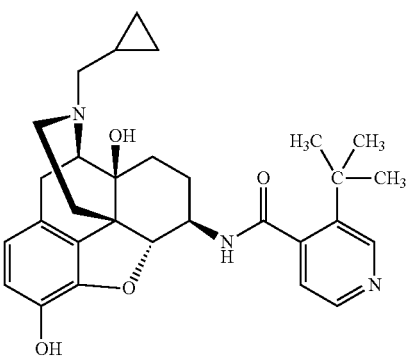
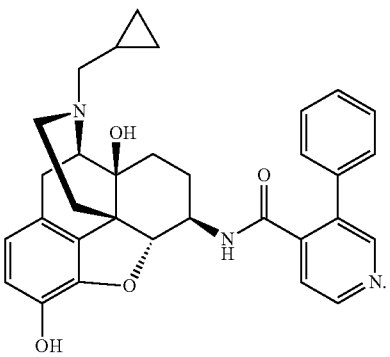
In another aspect, what is provided is a compound of the Formula Ib, a pharmaceutically acceptable salt, or a solvate thereof:

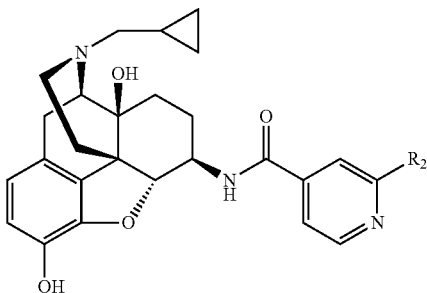

Formula Ib where, with respect to Formula I: n is 0; R1, R3 and R4 are H; and R2 is Cl, Br, CN, CH₃ or OCH₃.

In some aspects of the invention, the compound of Formula I is used to modulate opioid receptors.

In other aspects of the invention, the compound of Formula I is used to selectively interact with MOR.

In further aspects of the invention, the compound of Formula I acts as a modulator and is useful for the treatment of opioid use disorders, alcoholism, pain, and/or neurological disorders associated with opioid receptors.

As used herein, a "compound" of the invention includes all solvates, complexes, polymorphs, radiolabeled derivatives, tautomers, stereoisomers and optical isomers of the compounds of Formula I and salts thereof.

As used herein, an opioid use disorder (OUD) is defined as per the definition and description by the Centers for Disease Control (CDC), which states that in the DSM-5, OUD is defined as a problematic pattern of opioid use leading to clinically significant impairment or distress. OUD was previously classified as Opioid Abuse or Opioid Dependence and has also been referred to as "opioid addiction." Subjects with OUD exhibit a persistent desire or craving or unsuccessful efforts to cut down or control opioid use and spend a great deal of time in activities necessary to obtain the opioid, use the opioid, or recover from its effects. This often results in failure to fulfill major role obligations at work, school, or home. The subjects generally exhibit tolerance (either a need for markedly increased amounts of opioids to achieve intoxication or desired effect, or a markedly diminished effect with continued use of the same amount of an opioid) and/or withdrawal. Opioid withdrawal syndrome typically involves one or more of the following within minutes to several days after cessation of or reduction in opioid use: dysphoric mood; nausea or vomiting; muscle aches; lacrimation or rhinorrhea; pupillary dilation, piloerection; sweating; diarrhea; yawning; fever; or insomnia. Administration of one or more of the compounds described herein eliminates or lessens the severity of one or more of these symptoms.

As used herein, "neurological disorders associated with opioid receptors" include but are not limited to pain, alcoholism, other substance (e.g. cocaine, amphetamine, methamphetamine, etc.) use disorders, Parkinson's disease, schizophrenia, bipolar disease, etc.

Pharmaceutical Compositions and Administration

The compounds described herein are generally delivered (administered) in a pharmaceutical composition and the present invention encompasses such formulations/compositions. The pharmaceutical compositions generally comprise at least one of the disclosed compounds, i.e. one or more than one (a plurality of) different compounds (e.g. 2 or more) in a single formulation. The compositions also generally include a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the compounds are mixed with excipients which are pharmaceutically acceptable and compatible with the compounds, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as TWEEN® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed.

Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The pharmaceutical compositions may be administered in vivo by any suitable route including but not limited to: inoculation or injection (e.g. intravenous, intraperitoneal, intramuscular, subcutaneous, intra-aural, intraarticular, intramammary, and the like), topical application (e.g. on areas such as eyes, skin, in ears) and by absorption through epithelial or mucocutaneous linings (e.g., nasal, oral, vaginal, rectal, gastrointestinal mucosa, and the like). Other suitable means include but are not limited to: inhalation (e.g. as a mist or spray), orally (e.g. as a pill, capsule, liquid, etc.), intravaginally, intranasally, rectally, by ingestion of a food or probiotic product containing the compound(s), as eye drops, etc. In preferred embodiments, the mode of administration is oral or by injection.

An individual who is treated using the compounds described herein generally is a subject who is or has previously been addicted to opioids, either as the result of a legitimate medical use (e.g. the treatment of pain using a prescription opioid such as OXYCONTIN®, VICODIN®, etc.) and/or through recreational use. Thus, the person may be addicted to opioids, or may be at risk of becoming addicted due to, e.g., long-term usage, or may have previously been addicted and is in danger of a relapse. A family or personal history of substance abuse, including alcohol, medication and illicit drugs; a history of preadolescent sexual abuse; genetic predisposition; and personality factors, including ADD, OCD, bipolar disorder, schizophrenia and depression; may all lead to increased susceptibility to addiction, which can be addressed or averted by intervention using the compounds described herein.

The amount of a compound that is administered to an individual (who is usually a mammal, typically a human) will vary based on several factors, as will be understood by those of skill in the art. For example, the dose and frequency of administration may vary according to the gender, age, weight, general physical condition, ethnic background, etc. of the individual, as well as whether or not the individual has other diseases or conditions that might impinge on the treatment. Generally, the dose for a therapeutically effective amount will be in the range of from about 0.01 to about 1000 mg/kg of body weight. A therapeutically effective amount is generally an amount that ameliorates, lessens or improves at least one symptom of the disease/condition that is being treated, and this amount may also eradicate all symptoms of the disease/condition, i.e., it may cure the subject of the disease/condition. In particular, the subject may become entirely free of the craving for opioids and addiction or relapse may be prevented.

In addition, the compositions may be administered in conjunction with other treatment modalities such as substances that treat pain or addiction, for example: with opioids e.g. in methods where the amount of opioid that is administered is decreased over time and the amount of a compound described herein is increased over time to "wean" a subject from the opioid; with methadone, naltrexone and/or naloxone; with alternative pain medications such as NSAIDs (e.g. naproxen, ibuprofen, aspirin, acetaminophen), steroids, etc.; with alternative therapeutic measures that address pain such as acupuncture, meditation, etc.; and/or therapeutic measures to address mental conditions (depression, anxiety, etc.) such as psychiatric drugs, counseling, etc.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Results and Discussion

In designing the third generation NAP derivatives described herein, substitutions with different electronic, bulky, steric, and hydrophobic properties were introduced at the 3' position of the pyridyl ring (R) in the structure shown below:

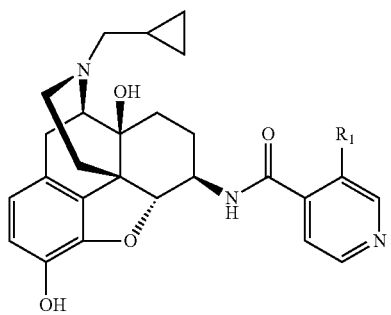

Twelve new NAP derivatives were synthesized (Table 1).

TABLE 1

| R1 groups at the 3' position of the pyridyl ring | |
|---|---|
| Compounds | R1 |
| 1 | F |
| 2 | CN |
| 3 | NO$_2$ |
| 4 | CF$_3$ |
| 5 | COOH |
| 6 | COOCH$_3$ |
| 7 | C$_2$H$_5$ |
| 8 | Isobutyl |
| 9 | Cyclopentyl |
| 10 | Cyclohexyl |

TABLE 1-continued

| R1 groups at the 3' position of the pyridyl ring | |
|---|---|
| Compounds | R1 |
| 11 | Cycloheptyl |
| 12 | Phenyl |

Chemistry

Compounds 1-6 were derivatives with electron-withdrawing groups at the 3' position on the pyridyl ring with a corresponding increment in size of the substituents. Compounds 7-12 were derivatives with electron-donating groups at the 3' position on the pyridyl ring with different bulkiness. For compounds 1-3, 9 and 12, the 3'-substituted pyridyl carboxylic acids were from commercial sources. For compounds 4-8, 10 and 11, the 3'-substituted pyridyl carboxylic acids were prepared as shown in Scheme 1 (Yakhontov, et al. *Chem. Heterocyclic Com.* 1967, 3, 829-831; Xin, *J. Chem. Res.* 2008, 2008, 412-415; Okawa, et al. *J. Med. Chem.* 2017, 60, 6942-6990).

Scheme 1. The synthesis of 3'-substituted pyridyl carboxylic acids for the newly designed NAP derivatives.

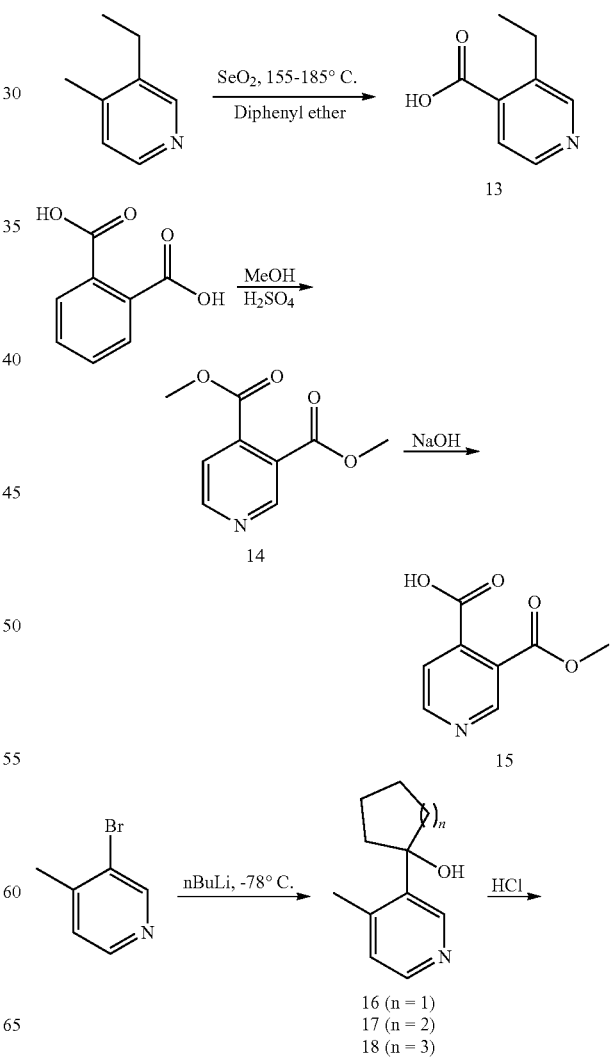

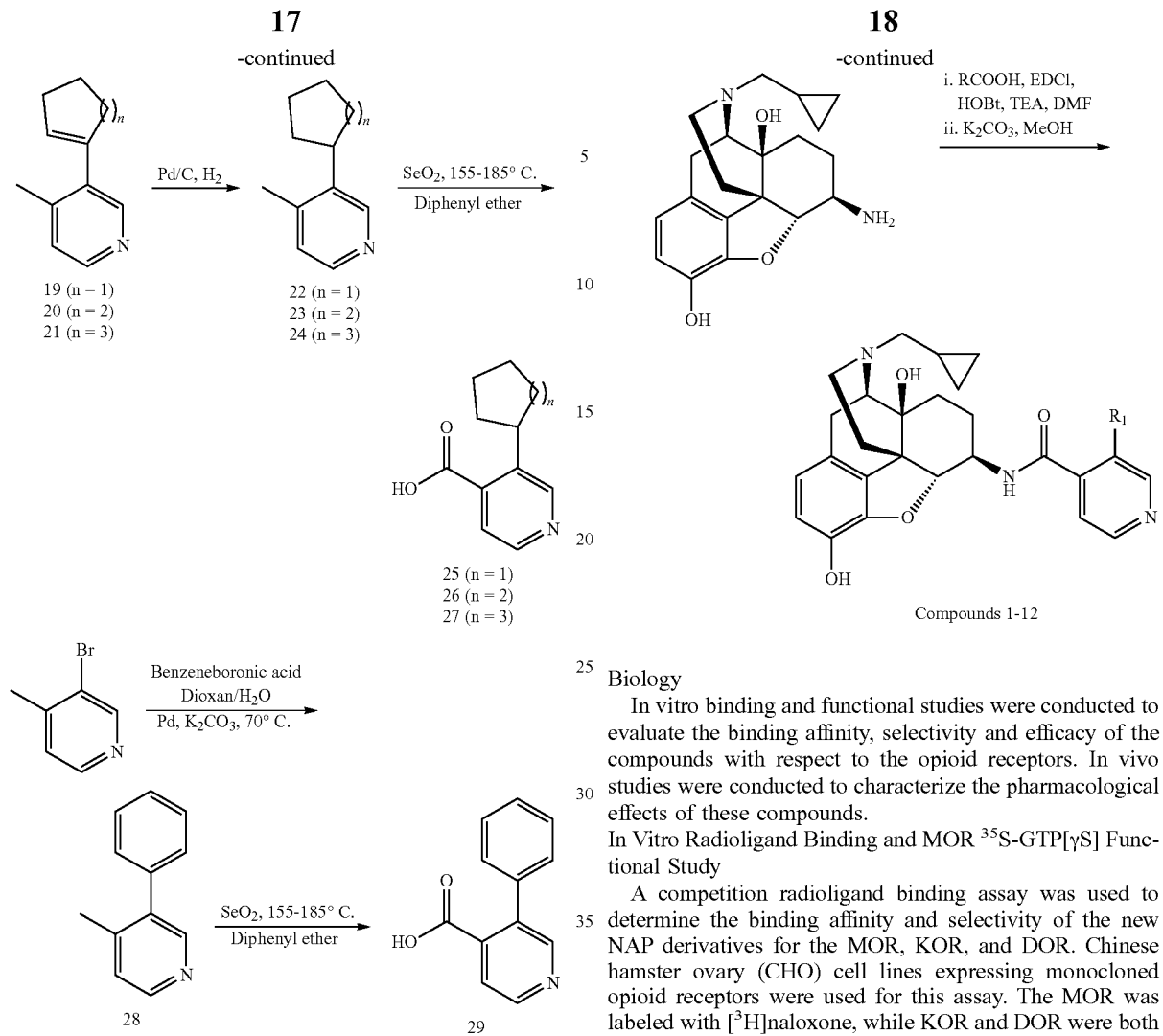

Biology

In vitro binding and functional studies were conducted to evaluate the binding affinity, selectivity and efficacy of the compounds with respect to the opioid receptors. In vivo studies were conducted to characterize the pharmacological effects of these compounds.

In Vitro Radioligand Binding and MOR $^{35}$S-GTP[γS] Functional Study

A competition radioligand binding assay was used to determine the binding affinity and selectivity of the new NAP derivatives for the MOR, KOR, and DOR. Chinese hamster ovary (CHO) cell lines expressing monocloned opioid receptors were used for this assay. The MOR was labeled with [$^3$H]naloxone, while KOR and DOR were both labeled with [$^3$H]diprenorphine.

As shown in Table 2, the binding affinity of all the compounds maintained subnanomolar affinity to the MOR except compounds 6 and 8 which showed nanomolar binding affinity. Compared to the first- and second-generation lead compounds, NAP ($K_{i, MOR}$=0.37±0.07 nM) and NMP ($K_{i, MOR}$=0.58±0.25 nM), all the third-generation derivatives still maintained high binding affinity to the MOR. This indicated that the substituent groups with different electronic properties and sizes at 3' position on the pyridyl ring did not significantly affect the binding affinity of these derivatives to the MOR. However, it is worth noting that esterification of the carboxylic acid at the 3' position (compound 6) and introduction of an isobutyl group at the 3' position (compound 8) resulted in a significant reduction in MOR binding affinity. As we mentioned above, the features of substituents on the 3' position of pyridyl ring, such as the steric hindrance, electrostatic, and hydrophobic effects, would significantly effect on the binding affinity and selectivity of NAP derivatives to the three opioid receptors.[58] Compound 6 was an esterification product of compound 5. After esterification, the original ionic interactions between carboxylic moiety in compound 5 and basic residues in the binding pocket of the MOR would be weakened in compound 6 significantly so that the binding affinity of compound 6 to the MOR was reduced. Furthermore, the isobutyl group on the pyridyl ring of compound 8 may result in steric clashes or unfavorable interactions with hydrophilic residues in the In addition, 6β-naltrexamine was synthesized as reported previously (Li, et al. *J. Med. Chem.* 2009, 52, 1416-1427) with a yield of 58% (Scheme 2). Then, the 4'-pyridyl carboxylic acids were coupled with 6β-naltrexamine by EDCI/HOBt method (Yuan, et al. J. Med. Chem. 2012, 55, 10118-10129). After that, the reaction crudes were treated with K$_2$CO$_3$ to obtain compounds 1-12 with yields ranging from 23% to 65% (Scheme 2).

Scheme 2. The synthesis route of the third generation NAP derivatives (compounds 1-12).

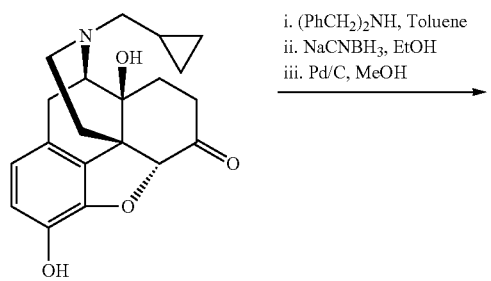

binding pocket that would decrease the binding affinity of compound 8 to the MOR. Interestingly, compared with compound 8, compounds 9-12 carried even bigger substituents on the pyridyl ring while maintained high binding affinities to the MOR at the subnanomolar level. One possible explanation of such an observation could be that some significant conformation changes induced by the much larger substituents on the pyridyl ring (compounds 9-11) may facilitate the compounds to interact with the binding pocket in the MOR in a more favorable fashion.

The selectivity of these compounds for the MOR over the DOR varied with different substituent groups at 3' position on the pyridyl ring. In general, derivatives with electron-withdrawing groups showed higher selectivity for the MOR over DOR than derivatives with electron-donating groups. For example, compounds 1-6 showed more than 30-fold selectivity for the MOR over the DOR, especially for compounds 1 (NFP, $\delta/\mu$=435.8) and 3 ($\delta/\mu$=562.4). Both compounds had similar selectivity for the MOR over the DOR as NMP ($\delta/\mu$=470). For the derivatives with electron-donating groups, compounds 7, 9, and 12 showed 50-134 fold selectivity for the MOR over the DOR while compounds 8, 10, and 11 showed 14-20 fold selectivity for the MOR over the DOR. Thus, it seemed that introduction of bulky and alkyl groups at position 3' on the pyridyl ring may reduce their selectivity for the MOR over the DOR.

On the KOR, there was a significant improvement in the binding affinity of all the compounds compared to NAP and NMP except for compound 8 which showed similar binding affinity to the KOR as to NAP and NMP. Compounds 1-7 and 9-12 maintained one-digit nanomolar or two-digit nanomolar binding affinity to the KOR. Thus, collectively, with substitution at 3' position on the pyridyl ring, the third generation NAP derivatives seemed to act as MOR/KOR dual-selective ligands.

TABLE 2

Radioligand binding results at MOR, KOR, and DOR and $^{35}$S-GTP[γS] functional assay at MOR for third generation NAP derivatives.

| Compounds | R1 | $K_i$(nM) MOR | $K_i$(nM) DOR | $K_i$(nM) KOR | Selectivity $\delta/\mu$ | Selectivity $\kappa/\mu$ | MOR $^{35}$S-GTP[γS] Binding EC$_{50}$ (nM) | % Emax of DAMGO |
|---|---|---|---|---|---|---|---|---|
| NTX[a] | N/A | 0.26 ± 0.02 | 117.1 ± 8.9 | 5.15 ± 0.26 | 450 | 20 | ND | 7.75 ± 0.20 |
| NAP[a] | 4-pyridyl | 0.37 ± 0.07 | 277.5 ± 8.0 | 60.7 ± 5.6 | 747 | 163 | 1.14 ± 0.38 | 22.72 ± 0.84 |
| 1(NFP) | 3-F-pyridyl | 0.36 ± 0.02 | 156.93 ± 7.81 | 4.80 ± 0.26 | 435.8 | 13.3 | 1.20 ± 0.19 | 34.97 ± 3.07 |
| 2(NYP) | 3-CN-pyridyl | 0.87 ± 0.09 | 46.29 ± 7.86 | 2.74 ± 0.47 | 53.2 | 3.1 | 1.28 ± 0.20 | 26.05 ± 0.74 |
| 3 | 3-NO$_2$-pyridyl | 0.17 ± 0.02 | 95.61 ± 5.90 | 4.46 ± 0.11 | 562.4 | 26.5 | 0.53 ± 0.01 | 39.10 ± 2.57 |
| 4 | 3-CF$_3$-pyridyl | 0.43 ± 0.01 | 61.79 ± 5.0 | 12.53 ± 0.89 | 143.7 | 29.1 | 1.38 ± 0.20 | 31.88 ± 3.39 |

TABLE 2-continued

Radioligand binding results at MOR, KOR, and DOR and $^{35}$S-GTP[γS] functional assay at MOR for third generation NAP derivatives.

| Compounds | R1 | K$_i$(nM) MOR | K$_i$(nM) DOR | K$_i$(nM) KOR | Selectivity δ/μ | Selectivity κ/μ | MOR $^{35}$S-GTP[γS] Binding EC$_{50}$ (nM) | MOR $^{35}$S-GTP[γS] Binding % Emax of DAMGO |
|---|---|---|---|---|---|---|---|---|
| 5 | 3-carboxy-pyridin-4-yl (COOH) | 0.76 ± 0.08 | 55.58 ± 6.02 | 2.43 ± 0.19 | 73.2 | 3.2 | 1.83 ± 0.18 | 29.27 ± 1.42 |
| 6 | 3-carboxylate-pyridin-4-yl (COO•) | 4.31 ± 0.29 | 137.31 ± 17.55 | 11.74 ± 1.15 | 31.9 | 2.7 | 13.40 ± 1.36 | 29.19 ± 0.84 |
| NMP[b] | 3-carboxylate-pyridin-4-yl (COO•) | 0.58 ± 0.25 | 273.6 ± 1.8 | 96.7 ± 12.2 | 470 | 166 | 1.52 ± 0.26 | 30.63 ± 0.55 |
| 7 | 3-ethyl-pyridin-4-yl | 0.32 ± 0.05 | 42.86 ± 8.27 | 9.18 ± 1.36 | 134.1 | 28.8 | 2.29 ± 0.28 | 41.65 ± 3.14 |
| 8 | 3-isobutyl-pyridin-4-yl | 7.20 ± 0.81 | 148.75 ± 15.96 | 75.63 ± 3.87 | 20.7 | 10.5 | 19.70 ± 2.37 | 27.30 ± 0.25 |
| 9 | 3-cyclopentyl-pyridin-4-yl | 0.60 ± 0.06 | 33.99 ± 3.99 | 8.16 ± 1.17 | 56.7 | 13.7 | 1.85 ± 0.16 | 56.67 ± 3.14 |
| 10 | 3-cyclohexyl-pyridin-4-yl | 0.78 ± 0.09 | 11.24 ± 1.91 | 3.32 ± 0.54 | 14.4 | 4.2 | 2.46 ± 0.30 | 51.59 ± 3.73 |

TABLE 2-continued

Radioligand binding results at MOR, KOR, and DOR and $^{35}$S-GTP[γS] functional assay at MOR for third generation NAP derivatives.

| Compounds | R1 | $K_i$(nM) MOR | $K_i$(nM) DOR | $K_i$(nM) KOR | Selectivity δ/μ | Selectivity κ/μ | MOR $^{35}$S-GTP[γS] Binding EC$_{50}$ (nM) | MOR $^{35}$S-GTP[γS] Binding % Emax of DAMGO |
|---|---|---|---|---|---|---|---|---|
| 11 | cycloheptyl-pyridyl | 0.93 ± 0.13 | 14.97 ± 2.44 | 5.16 ± 0.54 | 16.1 | 5.6 | 5.11 ± 0.16 | 48.32 ± 3.34 |
| 12 | phenyl-pyridyl | 0.63 ± 0.05 | 44.83 ± 3.70 | 3.42 ± 0.38 | 71.1 | 5.4 | 1.46 ± 0.18 | 44.42 ± 3.12 |

[a] reference 44a;
[b] reference 57a

The $^{35}$S-GTP[γS] functional assay was then conducted to determine the potency and relative efficacy of the synthesized compounds at the MOR. The potency was determined as the EC$_{50}$ while the efficacy was determined as the E$_{max}$ relative to DAMGO, a MOR full agonist. For the results, it seemed that all the compounds acted as partial agonists with moderate efficacy. Derivatives with electron-withdrawing groups (compounds 1-6) showed 20-40% MOR stimulation with one-digit nanomolar potency except compound 6. Meanwhile, derivatives with electron-donating groups (compounds 7-12) showed more than 40% efficacy with one or two-digit nanomolar potencies except compound 8 which had the lowest potency and MOR affinity.

In Vivo Tail Immersion Assay

Figure 1A:
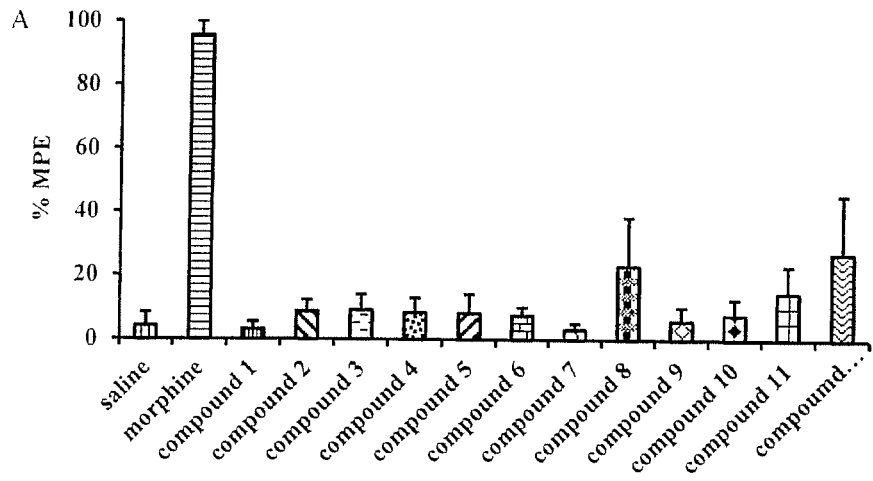
FIGS. 1A and B. Tail immersion assay results for the third generation NAP derivatives as agonist (A) and antagonist (B) in the presence of morphine in mice at a single dose of 10 mg/kg. Morphine (10 mg/kg) and saline were used as positive and negative controls (n=5, *** indicates P<0.005).
Figure 1B:
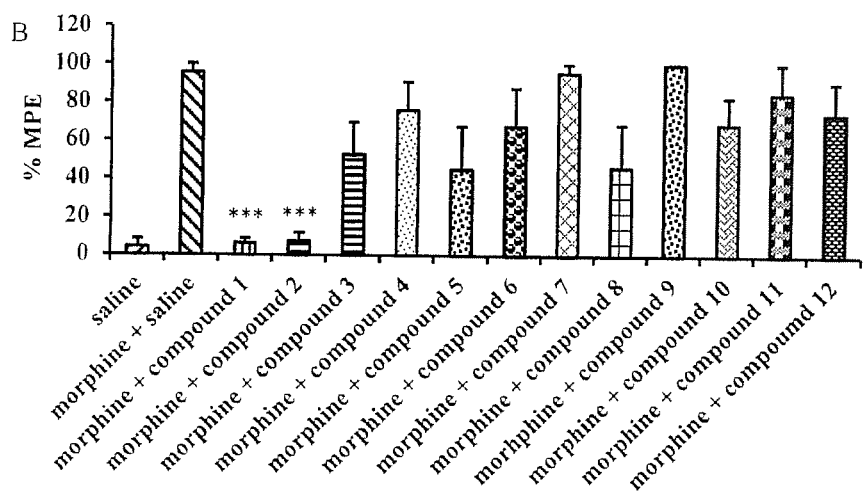
Figure 2A:
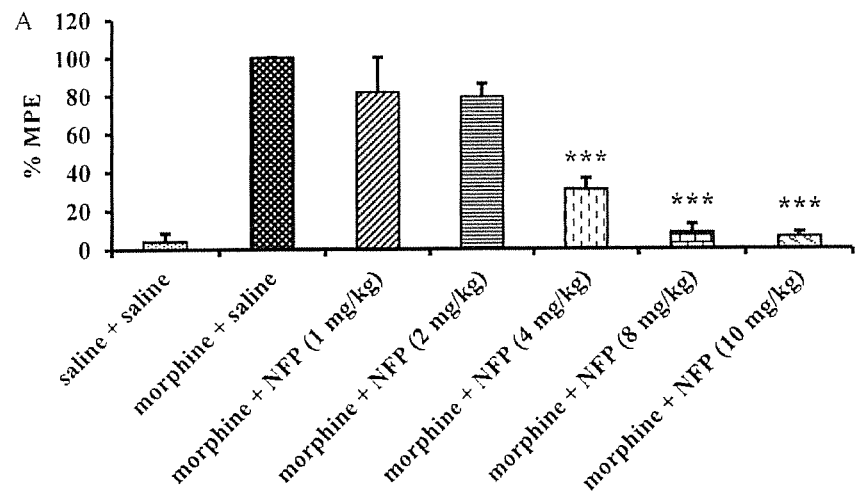
FIGS. 2A and B. Dose-response studies of NFP (A) and NYP (B) as antagonists in mice. Morphine (10 mg/kg) and saline were used as positive and negative controls (n=5, *** indicates P<0.005).
Figure 2B:
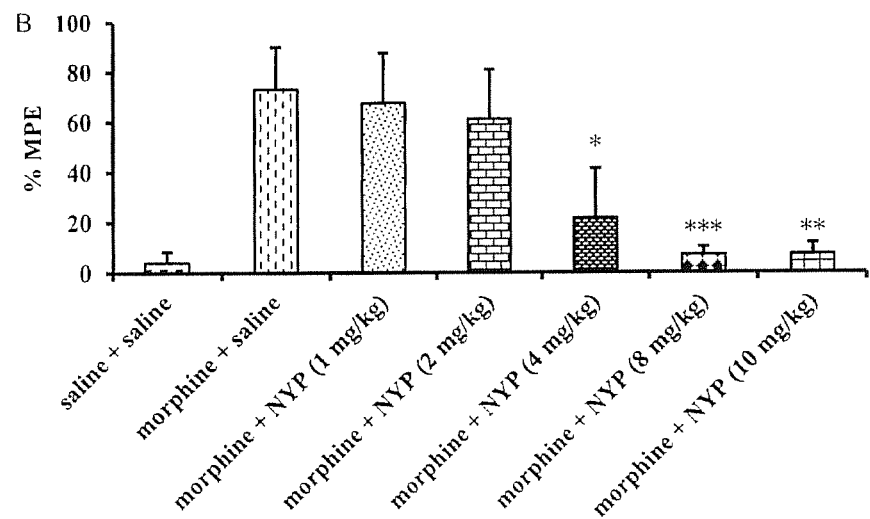

All the newly synthesized NAP derivatives were further assessed for their acute agonistic and/or antagonistic effects using the tail flick assay in mice as previously reported.[44, 57] Briefly, the derivatives were studied for their ability to produce antinociception or block the antinociception produced by morphine (10 mg/kg). As shown in FIG. 1A, none of these new derivatives showed significant antinociception compared to morphine at the same dose (10 mg/kg). However, when they were tested as antagonists at the same dose (FIG. 1B, 10 mg/kg), compounds 1 (NFP) and 2 (NYP) antagonized morphine's antinociception effect significantly. The percent maximum possible effects (% MPEs) of morphine (10 mg/kg) in the presence of NFP and NYP (10 mg/kg) were only 6.2±2.4% and 7.8±5.4%, respectively. The antagonism of NFP and NYP were shown to be dose-dependent (FIGS. 2A and 2B). In contrast to NFP and NYP, other NAP derivatives did not significantly block morphine's antinociception at the tested doses of 10 mg/kg. These results suggested that NFP and NYP had the ability to cross the blood brain barrier (BBB) and block the analgesic effect of morphine in CNS.

Two third generation NAP derivatives, NFP and NYP crossed the BBB and antagonized morphine's antinociception, while NAP was identified as a P-glycoprotein substrate and failed to cross the BBB effectively. Apparently, introduction of fluoro and nitrile groups on the pyridyl ring may play an important role in improving their CNS penetration. It is understood that about 5-15% of drugs on the market are fluorinated compounds[59, 60] and it has been shown that these compounds have improved metabolic stability and physicochemical properties.

Meanwhile fluorination seems to enhance the CNS penetration ability of non-CNS drugs and the efflux function of P-glycoprotein.[61,55] This may help explain why NFP crossed the BBB while NAP did not.[61] In addition, it has been reported that introducing nitrile groups may also enhance metabolic stability and improve hydrogen bonding interactions with residues in the orthosteric binding site of protein targets.[62] Currently, there are at least 30 drugs containing nitrile groups on the market and more than 20 drug candidates containing nitrile groups under clinical trials.[62] An example of such a drug is piritramide, an opioid analgesic which crosses the BBB and is used for post-operation pain like morphine.[63]

In Vivo Withdrawal Study

Figure 3A:
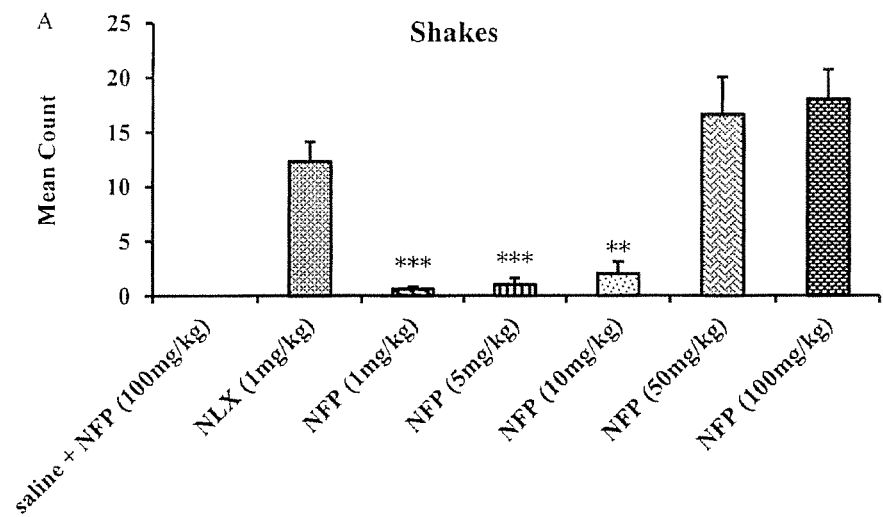
FIG. 3A-C. In vivo withdrawal study of NFP in morphine-pelleted mice (n=5). The first column in each figure represents the withdrawal effects of NFP in placebo-pelleted mice while the second to the seventh show the withdrawal effects of naloxone (1 mg/kg) and NYP in morphine-pelleted mice. (n=5, * means P<0.05,  means P<0.005, * indicates P<0.0005)
Figure 3B:
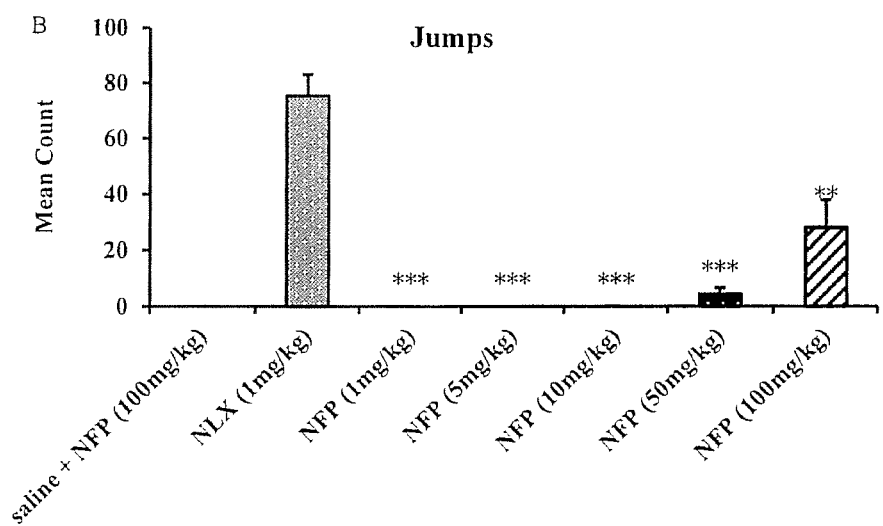
Figure 3C:
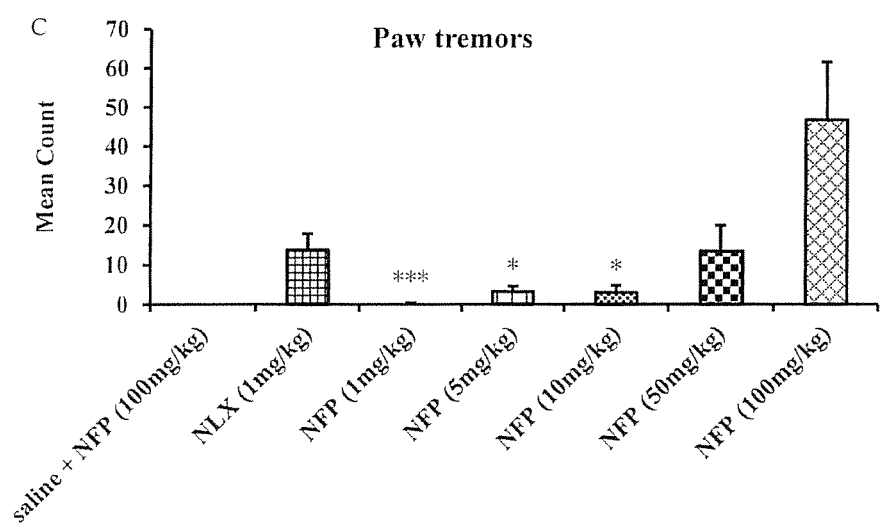
Figure 4A:
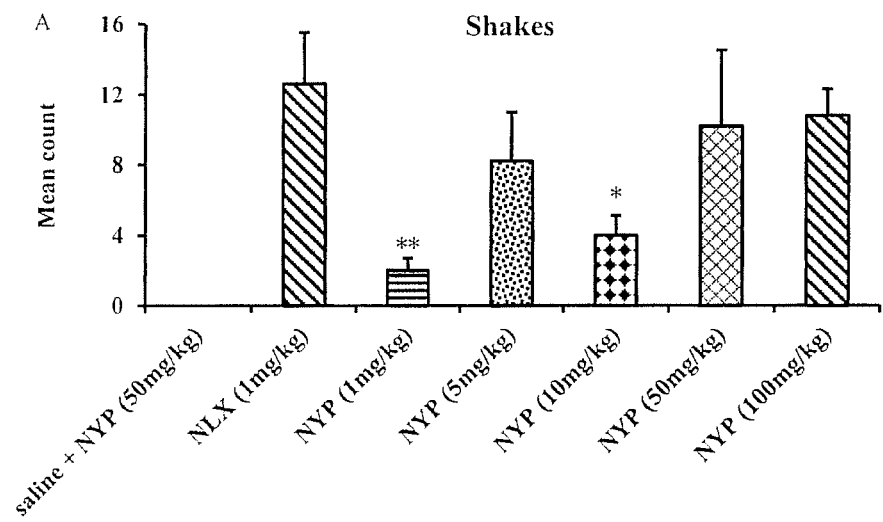
FIG. 4A-C. In vivo withdrawal study of NYP in morphine-pelleted mice (n=5). The first column in each figure represents the withdrawal effects of NYP in placebo-pelleted mice while the second to the seventh show the withdrawal effects of naloxone (1 mg/kg) and NYP in morphine-pelleted mice. (n=5, * indicates P<0.05,  indicates P<0.005, * indicates P<0.0005)
Figure 4B:
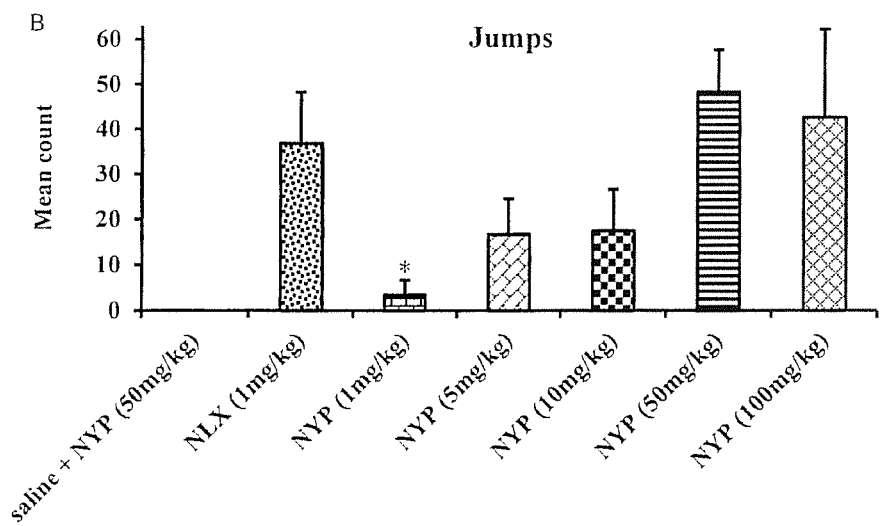
Figure 4C:
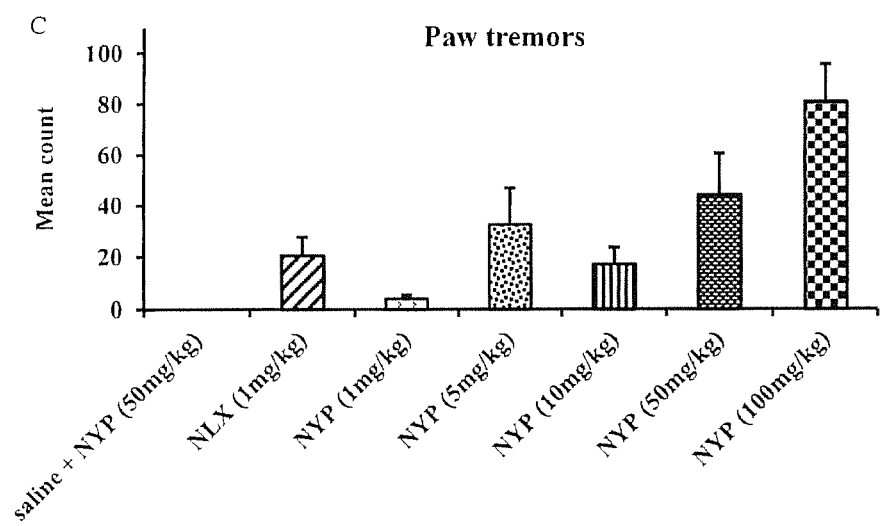

Opioid antagonists such as naloxone and naltrexone have been applied to reverse the effects of opioid agonists in cases of opioid overdose and in opioid addiction treatments. However, it has been shown that naloxone and naltrexone produce significant withdrawal symptoms when administered to addicts on opioid agonists, and that limits their use in opioid addiction treatments.[64] Since NFP and NYP were identified as opioid antagonists in vivo, a withdrawal study was conducted using morphine-pelleted mice to determine whether these two compounds produced withdrawal effects similar to naloxone. In this study, somatic symptoms of opioid withdrawal (shakes, jumps, and paw tremors) were quantified over a period of 20 minutes.[55] As shown in FIG. 3, NFP produced significantly fewer wet dog shakes, jumps, and paw tremors at 10 mg/kg than naloxone at 1 mg/kg. Meanwhile, at much higher doses (50 and 100 mg/kg) NFP produced wet dog shakes (FIG. 3A) and paw tremors (FIG. 3C), but not significantly different from those of naloxone at 1 mg/kg. More interestingly, NFP at a high dose of 50 mg/kg still produced significantly fewer jumps (FIG. 3B) than naloxone at 1 mg/kg. NYP, on the other hand, produced significantly fewer wet dog shakes and jumps at 1 mg/kg than naloxone at 1 mg/kg, but at doses 5 mg/kg and higher it produced wet dog shakes (FIG. 4A) and jumps (FIG. 4B) similar to naloxone at 1 mg/kg. Also, NYP produced similar paw tremors (FIG. 4B) at 1 mg/kg similar to naloxone at 1 mg/kg.

These results suggest that NFP has fewer significant withdrawal effects compared to naloxone. Taken together, the in vitro and in vivo results obtained for NFP suggest that NFP is a MOR/KOR ligand with the potential to be applied in opioid addiction treatments.

Figure 5A:
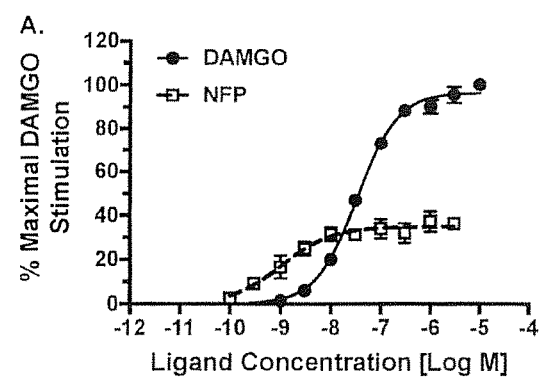
FIGS. 5A and B. MOR partial agonism and antagonism by NFP in mMOR-CHO cells. Ligand concentration-effect for stimulation of [$^{35}$S]GTPγS binding in membranes from mMOR-CHO cells were determined alone (A) or in the presence of 0.3 μM DAMGO (B). Data are mean±SEM (n=4-5) of the percentage of maximal stimulation (produced by a maximally-effective DAMGO concentration of 0.3 μM).
Figure 5B:
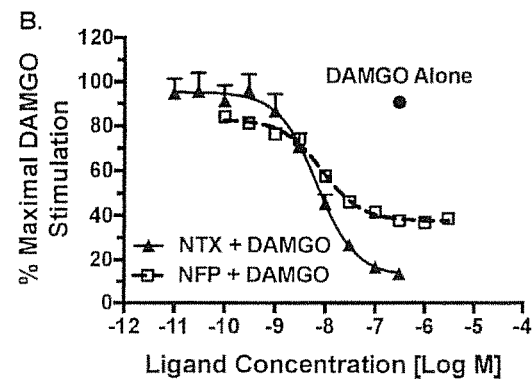

We then further characterized NFP's partial agonism and antagonism via concentration-effect curves for stimulation of [$^{35}$S]GTPγS binding in mMOR-CHO cells by NFP and DAMGO alone (FIG. 5A) in comparison to NFP curves in the presence in an EC90 DAMGO concentration (FIG. 5B). Naltrexone was examined as a positive control for MOR antagonism (FIG. 5B). Relative to DAMGO (normalized $E_{max}$=100±2.6% and $EC_{50}$=32.5±1.1 nM), NFP was a partial agonist with an $E_{max}$ value of 34.9±1.5% and $EC_{50}$ value of 1.21±0.19 nM, in agreement with our initial screening results (Table 1). In the presence of 0.3 μM DAMGO, NFP produced a concentration-dependent inhibition of DAMGO-stimulated [$^{35}$S]GTPγS binding, achieving maximal inhibition (minimum) at 37.7±1.5% of the maximal stimulation produced by DAMGO. Similarly, naltrexone produced concentration-dependent inhibition, with maximal inhibition at 12.8±0.4% of maxima DMAGO stimulation. Functional $K_i$ values were then calculated from these data. NFP and naltrexone inhibited DAMGO-stimulated [$^{35}$S]GTPγS binding with $K_1$ values of 0.86±0.09 and 0.67±0.05 nM, similar to their $K_1$ values for MOR binding (Table 1). NFP had a relative efficacy that was approximately 35% of DAMGO and 3-fold that of naltrexone under these experimental conditions.

Modeling Study

As described above, NFP exhibited dual-selective binding affinity to the MOR and KOR. Meanwhile NFP displayed significant selectivity for the MOR over the DOR ($K_i$, δ/μ=435.8). To understand its selectivity profile to the opioid receptors, the antagonist-bound crystal structures of MOR (PDB ID: 4DKL)[64], KOR (PDB ID: 4DJH)[65] and DOR (PDB ID: 4EJ4)[66] were downloaded from Protein Data Bank http://www.rcsb.org and NFP was docked into the three receptors by GOLD 5.4 (not shown). The binding poses of NFP with the highest CHEM-PLP scores from the docking studies were chosen as the optimal binding poses of the ligand in the MOR, KOR, and DOR.

Similar to the lead compound NAP, NFP was designed and synthesized according to the 'message-address' concept where the 'message' moiety (epoxymorphinan moiety) was assumed to determine its efficacy and the 'address' moiety (pyridyl ring) to contribute to its selectivity (FIG. 6A). Comparing the binding poses of NFP in the MOR, KOR, and DOR with those of NAP, we found that the identical 'message' moiety of NFP and NAP bound with the same domain of the MOR, KOR, and DOR through similar interactions with the conserved residues in the three receptors. Basically, the epoxymorphinan moiety formed hydrophobic interactions with the conserved residues $M^{3.36}$, $W^{6.48}$ and $H^{6.52}$ (superscript numbers follow the Ballesteros-Weinstein numbering method for GPCRs[69]) and hydrogen bonding interactions with $Y^{3.33}$ (FIG. 6B). Meanwhile, an ionic interaction was formed between the conserved $D^{3.32}$ and the nitrogen atom at the 17-position of the epoxymorphinan moiety of NFP (not shown). Collectively, the interactions between the 'message' moiety (epoxymorphinan moiety) of NFP and the conserved residues seemed to have no significant influence on the selectivity of NFP to the MOR, KOR, and DOR.

The fluorine atom on the pyridyl ring ('address' moiety) of NFP is a strong electron withdrawing group which would weaken the capability of the nitrogen atom on the pyridyl ring of NFP to keep a proton compared to the case of NAP and NMP.[58] In consequence, the nitrogen atom on the pyridyl ring of NFP might form electrostatic interactions with the conserved residue $E229^{5.35}$ in the MOR, $D223^{5.35}$ in the KOR, and $D210^{5.35}$ in the DOR. In addition, the pyridyl ring of NFP could also form hydrophobic interactions with the conserved hydrophobic residue $L^{ECL2}$ and $F^{ECL2}$ (Table 3). Thus, the 'address' moiety (pyridyl ring) of NFP seemed to bind to the same domain (termed 'address' domain) in the MOR, KOR, and DOR. However, several non-conserved residues located at this 'address' domain ($T218^{ECL2}$, $T225^{5.31}$, and $L232^{5.38}$ in the MOR, $S211^{ECL2}$, $Y219^{5.31}$, and $M226^{5.38}$ in the KOR and $M199^{ECL2}$, $S206^{5.31}$, and $T213^{5.38}$ in the DOR, FIG. 6) could also form direct interactions with the 'address' moiety (pyridyl ring) of NFP.

TABLE 3

The measured shortest distances between atoms on critical amino acid residues and atoms on the ligands of NFP in the MOR, KOR, and DOR from docking studies.

| Complex | Atom of receptor | Atom of ligand | Distance (Å) |
|---|---|---|---|
| NFP/MOR | CB@T218$^{ECL2}$ | C55@NFP | 4.5 |
|  | CB@L219$^{ECL2}$ | C55@NFP | 3.9 |
|  | CE2@F221$^{ECL2}$ | C57@NFP | 3.9 |
|  | OE2@E229$^{5.35}$ | N56@NFP | 3.2 |
|  | CD2@L232$^{5.38}$ | C58@NFP | 5.2 |
| NFP/KOR | CB @S211$^{ECL2}$ | C55@NFP | 3.6 |
|  | OG@S211$^{ECL2}$ | N56@NFP | 3.1 |
|  | CG@L212$^{ECL2}$ | C58@NFP | 4.0 |
|  | CE2@F214$^{ECL2}$ | C57@NFP | 4.8 |
|  | OH@Y219$^{5.31}$ | N56@NFP | 2.9 |
|  | OD2@D223$^{5.35}$ | N56@NFP | 3.7 |
|  | CG@M226$^{5.38}$ | C58@NFP | 6.9 |
| NFP/DOR | CB@M199$^{ECL2}$ | C55@NFP | 3.6 |
|  | CG@L200$^{ECL2}$ | C58@NFP | 4.6 |
|  | CE2@F202$^{ECL2}$ | C57@NFP | 4.4 |
|  | OD1@D210$^{5.35}$ | N56@NFP | 4.7 |
|  | CG2@T213$^{5.38}$ | C58@NFP | 7.2 |

As the distances determined by modeling studies showed, the electrostatic interaction between the nitrogen atom on the pyridyl ring of NFP and $E229^{5.35}$ in the MOR was much stronger than those in the NFP/KOR and NFP/DOR complexes, which may help to explain the highest affinity of NFP to the MOR. For the NFP/KOR complex, the non-conserved $Y219^{5.31}$ and $S211^{ECL2}$ could also form hydrogen bond with the nitrogen atom on the pyridyl ring of NFP, which may facilitate the binding of NFP to the KOR. However, for the NFP/DOR complex, no additional interaction being observed between the 'address' moiety of NFP and the residues located in the 'address' domain of DOR except the weakest electrostatic one from D210[5.35] (Table 3). Overall, the different interactions between the 'address' moiety of NFP and the 'address' domain of the MOR, KOR, and DOR helped explain the different binding affinities observed for NFP in the three receptors.

Conclusions

Based on previous studies in our group, the third generation 6β-N-4'-pyridyl substituted naltrexamine derivatives were designed, synthesized and evaluated in both in vitro and in vivo assays. The in vitro competition assays showed that the third-generation compounds carrying varies substitutions at the 3' position of pyridyl ring carried a different selectivity profile than NAP. In that, the third-generation compounds were typically MOR/KOR dual-selective while NAP was highly MOR selective. Most of the new compounds retained their binding affinity to the MOR with subnanomolar level and one-digit nanomolar binding affinity to KOR. All of the compounds had low to medium efficacy at the MOR with one-digit nanomolar potencies. Among these derivatives, NFP and NYP significantly antagonized the antinociception produced by morphine in a dose dependent fashion. The in vivo withdrawal studies showed that NFP produced significantly less withdrawal symptoms than naloxone at similar doses. These findings indicate that NFP will be useful in treating opioid addition and abuse and can function as or in the development of MOR/KOR dual selective ligands for treating drug or alcohol addiction and abuse, particularly, opioid addiction and abuse.

Experimental

Chemistry
General Methods

Reagents were purchased from either Sigma-Aldrich or Alfa Aesar. TLC analyses were carried out on the Analtech Uniplate F254 plates. Chromatographic purification was conducted on silica gel column (230-400 mesh, Merck). $^1$H (400 MHz) and $^{13}$C (100 MHz) nuclear magnetic resonance (NMR) spectra were recorded at ambient temperature with tetramethylsilane as the internal standard on a Varian Mercury 400 MHz NMR spectrometer. Melting points were recorded with OptiMelt Automated Melting Point System (Fisher Scientific). IR spectra were obtained with NICO-LAT™ IS™10 instrument (Thermo Scientific). Applied Bio Systems 3200 Q trap with a turbo V source for TURBO-LONSPRAY™ was used for MS analysis. HPLC analysis was performed by a Varian ProStar 210 system on Agilent Microsorb-MV 100-5 C18 (250 mm×4.6 mm) at 210 nm with water/acetonitrile (25/75, 30/70 or 35/65, 0.01% TFA in water; Eluents A, B and C, respectively, in Table 4) at 0.8 mL/min over 30 min. The purity of the third generation NAP derivatives were determined by above analytical methods and their purity were identified as ≥95%.

TABLE 4

The HPLC analysis of compounds 1-12

| Compound Number | Retention Time (min) | Purity (%) | HPLC Eluent |
|---|---|---|---|
| 1 | 5.563 | 96.57 | A |
| 2 | 5.810 | 98.13 | A |
| 3 | 6.291 | 96.83 | B |
| 4 | 6.674 | 98.16 | C |
| 5 | 6.108 | 97.32 | C |
| 6 | 8.758 | 94.74 | C |

TABLE 4-continued

The HPLC analysis of compounds 1-12

| Compound Number | Retention Time (min) | Purity (%) | HPLC Eluent |
|---|---|---|---|
| 7 | 7.926 | 98.16 | C |
| 8 | 8.867 | 99.55 | C |
| 9 | 5.5842 | 97.47 | A |
| 10 | 5.934 | 95.63 | A |
| 11 | 10.425 | 95.99 | A |
| 12 | 6.695 | 99.50 | A |

General Procedure

N-(3-dimethylaminopropyl)-N'-ethylcarbodiimide hydrochloride (2.5 eq), hydrobenzotriazole (2.5 eq), 4 Å molecular sieves, and trimethylamine (5 eq) were added to a solution of the carboxylic acid (2.5 eq) in DMF on an ice-water bath under $N_2$ protection. After 30 min, a solution of 6β-naltrexamine (1 eq) in DMF was added dropwise. The mixture was kept stirring overnight at room temperature and filtered the next day. The filtrate was then concentrated under reduced pressure to remove the solvent. The residue was dissolved in MeOH and potassium carbonate (2 eq) was added to the mixture. The reaction mixture was stirred overnight at room temperature. Next day, the mixture was concentrated and the residue was purified with silica gel column to obtain the target compound.

17-Cyclopropylmetyl-3,14β-dihydroxy-4,5α-epoxy-6β-[(3'-fluoro-4'-pyridyl) acetamido]morphinan (Compound 1, NFP)

Compound 1 was synthesized as shown in the general procedure with a yield of 48%.

$^1$H NMR (400 MHz, CDCl$_3$) δ 8.94 (s, 1H), 8.74 (d, J=8.08 Hz, 1H), 8.58 (m, 1H), 8.43 (m, 1H), 7.46 (t, J=5.6 Hz, 1H), 6.51 (d, J=8.1 Hz, 1H), 6.45 (d, J=8.1 Hz, 1H), 4.77 (s, 1H), 4.45 (d, J=8.1 Hz, 1H), 3.52 (m, 1H), 2.90 (m, 2H), 2.47 (m, 2H), 2.21 (m, 2H), 2.02 (m, 1H), 1.87 (m, 1H), 1.73 (m, 1H), 1.48 (m, 1H), 1.37 (m, 1H), 1.21 (m, 1H), 1.15 (m, 1H), 0.73 (m, 1H), 0.35 (m, 2H), 0.01 (m, 2H).

$^{13}$C NMR (100 MHz, DMSO-d$_6$) δ 161.54, 156.46, 153.90, 146.23, 146.18, 142.06, 140.46, 139.10, 138.86, 131.24, 131.05, 130.93, 123.52, 123.23, 118.47, 117.12, 90.39, 69.52, 61.75, 58.38, 51.90, 47.06, 43.66, 30.32, 29.97, 24.33, 22.19, 9.22, 3.65, 3.52.

$^{19}$F NMR (75 MHz, DMSO-d$_6$) δ −192.29.

IR (diamond, cm$^{-1}$) $V_{max}$ 2942.19, 2829.33, 1655.64, 1529.02, 1487.78, 1454.25, 1416.41, 1322.93, 1238.29, 1204.29, 1186.88, 1152.58, 1131.78, 1100.14, 1034.82, 1017.27, 985.87, 942.11, 919.01, 898.28, 882.36, 799.14, 785.35, 763.19, 746.38, 667.00.

Mass Spectrum $C_{26}H_{28}FN_3O_4$ m/z calc. 465.2064 obs. 466.2159 [M+H]$^+$. Mp 277.6-280.6° C.

17-Cyclopropylmetyl-3,14β-dihydroxy-4,5α-epoxy-6β-[(3'-cyano-4'-pyridyl) acetamido]morphinan (Compound 2, NYP)

Compound 2 was synthesized as shown in the general procedure with a yield of 48%.

$^1$H NMR (400 MHz, DMSO-d$_6$) δ 9.15-9.13 (m, 2H), 8.94 (s, 1H), 7.92 (d, J=3.6 Hz, 1H), 7.44 (s, 1H), 7.31 (s, 1H), 7.18 (s, 1H), 6.77 (d, J=8.08 Hz, 1H), 6.69 (d, J=8.08 Hz, 1H), 5.06 (d, J=8.24 Hz, 1H), 3.38-3.33 (m, 3H), 3.11-3.06 (m, 3H), 2.9 (m, 1H), 1.93-1.90 (m, 1H), 1.51-1.43 (m, 3H), 1.10-1.09 (m, 1H), 0.67 (m, 1H), 0.60 (m, 1H), 0.51 (m, 1H), 0.42 (m, 1H).

$^{13}$C NMR (100 MHz, DMSO-$d_6$) δ 167.45, 167.09, 156.63, 144.66, 142.37, 142.15, 139.45, 129.84, 125.95, 121.26, 120.30, 118.68, 117.50, 87.36, 70.14, 62.25, 57.32, 52.30, 47.03, 46.66, 30.59, 27.74, 23.65, 21.51, 6.32, 5.70, 3.24.

IR (diamond, cm$^{-1}$) V$_{max}$ 3111.05, 2087.54, 1721.23, 1626.30, 1501.34, 1467.64, 1371.61, 1322.77, 1079.34, 1031.03, 858.34, 731.40.

Mass Spectrum $C_{27}H_{28}N_4O_4$ m/z calc. 472.2111 obs. 474.2049 [M+2H]$^+$. Mp 222.8-224.5° C.

17-Cyclopropylmetyl-3,14β-dihydroxy-4,5α-epoxy-6β-[(3'-nitro-4'-pyridyl) acetamido]morphinan (Compound 3)

Compound 3 was synthesized as shown in the general procedure with a yield of 52%.

$^1$H NMR (400 MHz, DMSO-$d_6$) δ 9.16 (s, 1H), 8.94 (m, 1H), 8.87 (m, 1H), 7.53 (m, 1H), 6.50 (d, J=8.1 Hz, 1H), 6.44 (d, J=8.1 Hz, 1H), 4.35 (d, J=7.8 Hz, 1H), 3.42 (m, 1H), 2.90 (m, 2 H), 2.49 (m, 2H), 2.22 (m, 2H), 2.01 (m, 1H), 1.88 (m, 1H), 1.70 (m, 1H), 1.57 (m, 1H), 1.39 (m, 1H), 1.19 (m, 2H), 0.73 (m, 1H), 0.35 (m, 2H), 0.01 (m, 2H).

$^{13}$C NMR (100 MHz, DMSO-$d_6$) δ 163.07, 154.58, 145.17, 142.56, 142.01, 140.49, 139.18, 131.16, 123.46, 122.82, 118.53, 117.14, 90.25, 69.52, 61.69, 58.32, 54.85, 52.11, 47.04, 43.66, 30.28, 29.84, 23.57, 22.18, 9.11, 3.68, 3.48.

IR (diamond, cm$^{-1}$) V$_{max}$ 3072.08, 2952.94, 2820.03, 1681.02, 1639.45, 1615.13, 1567.61, 1550.22, 1531.35, 1451.63, 1393.77, 1357.98, 1348.34, 1329.88, 1277.14, 1262.58, 1253.30, 1241.33, 1227.99, 1189.63, 1147.14, 1121.29, 1035.17, 984.65, 945.33, 931.99, 922.82, 915.19, 896.65, 882.54, 858.32, 828.95, 806.17, 763.88, 740.60, 732.83, 721.00, 672.69.

Mass Spectrum $C_{26}H_{28}N_4O_4$ m/z calc. 492.2009 obs. 493.2087 [M+H]$^+$. Mp 266.46-269° C.

17-Cyclopropylmetyl-3,14β-dihydroxy-4,5α-epoxy-6β-[(3'-trifluromethyl-4'-pyridyl) acetamido]morphinan (Compound 4)

Compound 4 was synthesized as shown in the general procedure with a yield of 51%.

$^1$H NMR (400 MHz, DMSO-$d_6$) δ 9.38 (s, 1H), 9.04 (s, 1H), 9.02 (m, 1H), 8.98 (m, 1H), 7.56 (m, 1H), 6.75 (d, J=8.1 Hz, 1H), 6.66 (d, J=8.1 Hz, 1H), 4.62 (d, J=8.1 Hz, 1H), 3.38 (m, 1H), 3.04 (m, 2H), 2.83 (m, 2H), 2.43 (m, 2H), 2.16 (m, 1H), 1.82 (m, 2H), 1.84 (m, 1H), 1.62 (m, 1H), 1.41 (m, 1H), 0.86 (m, 1H), 0.76 (m, 2H), 0.53 (m, 2H).

$^{13}$C NMR (100 MHz, DMSO-$d_6$) δ 164.68, 154.10, 147.20, 143.25, 142.09, 141.39, 129.55, 123.01, 122.22, 121.83, 121.17, 119.33, 117.98, 89.34, 69.64, 61.60, 60.67, 51.54, 45.67, 32.18, 29.30, 27.69, 22.97, 21.96, 13.95, 5.71, 5.05.

$^{19}$F NMR (75 MHz, DMSO-$d_6$) δ−57.80.

IR (diamond, cm$^{-1}$) V$_{max}$: 3216.30, 2935.48, 2831.91, 1676.72, 1607.94, 1557.26, 1502.39, 1471.37, 1452.47, 1422.76, 1377.05, 1328.16, 1281.32, 1194.14, 1132.27, 1081.31, 1054.16, 1038.57, 1027.12, 999.69, 982.16, 927.80, 890.56, 858.47, 821.56, 785.26, 720.13, 691.36, 675.16.

Mass Spectrum $C_{27}H_{28}F_3N_3O_4$ m/z calc. 515.2032 obs. 516.2089 [M+H]$^+$. Mp 224.9-227.5° C.

17-Cyclopropylmetyl-3,14β-dihydroxy-4,5α-epoxy-6β-[(3'-carboxyl-4'-pyridyl) acetamido]morphinan (Compound 5)

Compound 5 was synthesized as shown in the general procedure with a yield of 23%.

$^1$H NMR (400 MHz, DMSO-$d_6$) δ 9.14 (d, J=0.84 Hz, 1H), 9.12 (d, J=4.76 Hz, 1H), 8.99 (s, 1H), 7.91 (d, J=1.08 Hz, 1H), 7.90 (d, J=0.92 Hz, 1H), 6.62-6.52 (m, 2H), 4.99 (d, J=8.08 Hz, 1H), 4.92 (s, 1H), 3.91-3.82 (m, 1H), 3.16 (d, J=5.24 Hz, 1H), 3.03 (t, 2H), 2.97 (s, 1H), 2.63-2.60 (m, 1H), 2.57-2.53 (m, 1H), 2.40-2.30 (m, 2H), 2.24-2.18 (m, 1H), 2.02-1.95 (m, 1H), 1.59-1.55 (m, 1H), 1.18-1.44 (m, 1H), 1.41-1.34 (m, 1H), 1.26-1.23 (m, 1H), 0.87-0.82 (m, 1H), 0.48-0.46 (m, 2H), 0.13-0.11 (m, 2H).

$^{13}$C NMR (100 MHz, DMSO-$d_6$) δ 167.65, 167.25, 156.53, 144.44, 141.89, 141.13, 139.43, 125.90, 119.61, 117.53, 88.10, 70.04, 62.06, 58.80, 52.80, 49.03, 48.08, 44.14, 31.23, 22.66, 4.26, 4.00.

IR (diamond, cm$^{-1}$) V$_{max}$ 3345.73, 3039.98, 2478.91, 2079.72, 1782.60, 1725.96, 1651.70, 1630.27, 1614.51, 1556.21, 1505.72, 1455.55, 1398.02, 1361.26, 1263.68, 728.87, 708.62 Mass Spectrum $C_{27}H_{29}N_3O_6$ m/z calc. 491.2056 obs. 474.2033 [M-CH$_3$]$^+$. Mp 271.2-273.7° C.

17-Cyclopropylmetyl-3,14β-dihydroxy-4,5α-epoxy-6β-[(3'-methyl formate-4'-pyridyl) acetamido]morphinan (Compound 6)

Compound 6 was synthesized as shown in the general procedure with a yield of 32%.

$^1$H NMR (400 MHz, DMSO-$d_6$) δ 9.16 (s, 1H), 9.12 (s, 1H), 9.08 (s, 1H), 9.00 (d, J=3.68 Hz, 1H), 7.91 (d, J=3.68 Hz, 1H), 7.76 (d, J=3.52 Hz, 1H), 7.31 (s, 1H), 7.26 (d, d, J=8.24 Hz, 1H), 7.00 (d, J=8.24 Hz, 1H), 5.16 (7.26 (d, J=8.24 Hz, 1H)), 3.83 (s, 3H), 3.55 (s, 1H), 3.50 (s, 1H), 3.36-3.35 (m, 1H), 3.27-3.24 (s, 1H), 3.23 (s, 2H), 3.16-3.12 (m, 1H), 2.95 (m, 1H), 2.66-2.63 (m, 1H), 1.99-1.95 (m, 1H), 1.57-1.44 (m, 3H), 1.23-1.19 (m, 1H), 1.13 (m, 1H), 0.69 (m, 1H), 0.62 (m, 1H), 0.54 (m, 1H), 0.45 (m, 1H).

$^{13}$C NMR (100 MHz, DMSO-$d_6$) δ 167.04, 165.51, 163.83, 156.57, 154.31, 150.66, 146.23, 144.61, 139.14, 134.01, 131.22, 130.14, 123.75, 122.67, 120.93, 117.47, 89.86, 70.03, 61.97, 57.38, 53.57, 52.41, 49.14, 46.62, 30.53, 27.58, 24.12, 21.11, 6.29, 5.70, 3.29.

IR (diamond, cm$^{-1}$) V$_{max}$ 3554.62, 2953.39, 2088.05, 1716.47, 1633.27, 1557.57, 1489.97, 1446.28, 1367.76, 1290.11, 1263.40, 1234.61, 1193.08, 1152.84, 1128.11, 1101.15, 1076.56, 1032.71, 995.14, 960.71, 938.56, 914.77, 892.11, 855.03, 834.94, 797.66, 780.76, 732.58, 685.21, 662.07

Mass Spectrum m/z calc. $C_{28}H_{31}N_3O_6$ 505.2213 obs. 506.2227 [M+H]$^+$. Mp 210.5-212.3° C.

17-Cyclopropylmetyl-3,14β-dihydroxy-4,5α-epoxy-6β-[(3'-ethyl-4'-pyridyl) acetamido]morphinan (Compound 7)

Compound 7 was synthesized as shown in the general procedure with a yield of 61%.

$^1$H NMR (400 MHz, DMSO-$d_6$) δ 9.00 (s, 1H), 8.50 (m, 2H), 7.25 (m, 1H), 6.70 (d, J=8.1 Hz, 1H), 6.54 (d, J=8.1 Hz, 1H), 4.53 (d, J=7.8 Hz, 1H), 3.61 (m, 1H), 3.01 (m, 2H), 2.74 (q, J=7.6 Hz, 2H), 2.56 (m, 2H), 2.29 (m, 2H), 2.12 (m,

1H), 2.00 (m, 1H), 1.82 (m, 1H), 1.62 (m, 1H), 1.48 (m, 1H), 1.34 (m, 1H), 1.25 (m, 1H), 1.16 (t, J=7.6 Hz, 3H), 0.84 (m, 1H), 0.47 (m, 2H), 0.12 (m, 2H).

$^{13}$C NMR (100 MHz, DMSO-d$_6$) δ 166.80, 150.49, 147.32, 143.38, 142.17, 140.54, 135.81, 131.33, 123.50, 120.89, 118.39, 117.10, 90.38, 69.58, 61.74, 58.37, 54.86, 51.53, 47.05, 43.68, 30.09, 24.32, 23.14, 22.19, 15.54, 9.22, 3.65, 3.51.

IR (diamond, cm$^{-1}$) V$_{max}$ 3307.45, 3084.08, 2946.81, 2931.57, 2822.35, 1659.73, 1592.75, 1530.90, 1503.18, 1471.36, 1454.36, 1431.17, 1404.97, 1368.65, 1322.47, 1260.16, 1239.39, 1227.39, 1190.27, 1154.54, 1128.18, 1114.19, 1096.93, 1082.03, 1059.66, 1036.40, 1028.24, 974.96, 932.47, 922.72, 915.97, 899.73, 877.40, 855.23, 818.18, 799.14, 784.30, 761.82, 744.37, 709.36, 675.07.

Mass Spectrum m/z calc. C$_{28}$H$_{33}$N$_3$O$_4$ 475.2471 obs. 476.2539 [M+H]$^+$. Mp 238.6-241.3° C.

17-Cyclopropylmetyl-3,14β-dihydroxy-4,5α-epoxy-6β-[(3'-isobutyl-4'-pyridyl) acetamido]morphinan (Compound 8)

Compound 8 was synthesized as shown in the general procedure with a yield of 48%.

$^1$H NMR (400 MHz, CDCl$_3$) δ 8.61 (d, J=5.04 Hz, 1H), 8.58 (s, 1H), 8.48-8.46 (m, 2H), 7.86 (d, J=5.04 Hz, 1H), 7.23 (d, J=4.92 Hz, 1H), 6.96 (d, J=8.16 Hz, 1H), 6.74 (d, J=8.20, 1H), 4.56 (d, J=4.80 Hz, 1H), 4.27-4.21 (m, 1H), 3.15 (s, 1H), 3.11 (s, 1H), 2.90-2.86 (m, 1H), 2.68-2.66 (m, 2H), 2.41-2.39 (m, 1H), 2.27-2.25 (m, 1H), 1.96-1.85 (m, 1H), 1.65-1.63 (m, 1H), 1.26 (s, 1H), 0.93 (d, J=2.20 Hz, 2H), 0.91 (d, J=2.16 Hz, 2H), 0.84 (d, J=7.96 Hz, 6H), 0.57-0.55 (m, 2H), 0.16-0.15 (m, 2H).

$^{13}$C NMR (100 MHz, CDCl$_3$) δ 167.37, 164.01, 153.50, 152.53, 148.14, 143.75, 137.28, 136.07, 134.23, 132.66, 132.14, 123.90, 122.76, 120.83, 119.34, 92.94, 69.91, 62.25, 59.63, 49.70, 47.07, 43.86, 40.21, 39.46, 30.39, 30.21, 28.70, 23.25, 22.55, 4.19, 3.94, 0.13.

IR (diamond, cm$^{-1}$) V$_{max}$ 3212.54, 3055.22, 2957.95, 2869.52, 2580.83, 2089.08, 1756.35, 1659.98, 1633.88, 1446.95, 1257.27, 1234.91, 1057.99, 851.95, 772.04, 666.71.

Mass Spectrum m/z calc. C$_{30}$H$_{37}$N$_3$O$_4$ 503.2784 obs. 504.2653 [M+H]$^+$. Mp 195.5-197.8° C.

17-Cyclopropylmetyl-3,14β-dihydroxy-4,5α-epoxy-6β-[(3'-cyclopentanyl-4'-pyridyl) acetamido]morphinan (Compound 9)

Compound 9 was synthesized as shown in the general procedure with a yield of 58%.

$^1$H NMR (400 MHz, CDCl$_3$) δ 8.66 (s, 1H), 8.43 (m, 1H), 7.05 (m, 1H), 7.03 (m, 1H), 6.74 (d, J=8.1 Hz, 1H), 6.58 (2 d, J=8.1 Hz, 1H), 4.45 (d, J=7.8 Hz, 1H), 3.99 (m, 1H), 3.33 (m, 1H), 3.06 (m, 2H), 2.63 (m, 2H), 2.36 (m, 2H), 2.18 (m, 2H), 2.08 (m, 2H), 1.83 (m, 3H), 1.65 (m, 16H), 1.49 (m, 2H), 0.82 (m, 1H), 0.52 (m, 2H), 0.12 (m, 2H).

$^{13}$C NMR (100 MHz, MeOH-d$_4$) δ 170.58, 149.17, 147.62, 146.33, 143.88, 142.80, 140.26, 122.25, 120.57, 119.18, 92.20, 71.59, 64.10, 59.53, 53.32, 41.77, 35.59, 35.51, 31.29, 26.59, 25.02, 24.07, 5.35, 3.80.

IR (diamond, cm$^{-1}$) V$_{max}$ 3135.82, 3042.97, 2956.45, 2868.49, 1635.34, 1543.77, 1504.22, 1451.51, 1406.10, 1324.84, 1242.99, 1156.26, 1124.74, 1060.06, 1032.41, 1012.61, 986.31, 919.54, 855.36, 799.44, 781.28, 747.15, 677.37.

Mass Spectrum C$_{31}$H$_{37}$N$_3$O$_4$ m/z calc. 515.2784 obs. 516.2896 [M+H]$^+$. Mp 231.1-232.8° C.

17-Cyclopropylmetyl-3,14β-dihydroxy-4,5α-epoxy-6β-[(3'-cyclohexanyl-4'-pyridyl) acetamido]morphinan (Compound 10)

Compound 10 was synthesized as shown in the general procedure with a yield of 51%.

$^1$H NMR (400 MHz, CDCl$_3$) δ 8.66 (s, 1H), 8.46 (m, 1H), 7.11 (m, 1H), 6.89 (m, 1H), 6.74 (d, J=8.1 Hz, 1H), 6.58 (d, J=8.1 Hz, 1H), 4.43 (d, J=7.8 Hz, 1H), 4.06 (m, 1H), 3.19 (m, 1H), 2.91 (m, 2H), 2.63 (m, 2H), 2.36 (m, 2H), 2.18 (m, 2H), 1.85 (m, 5H), 1.74 (m, 1H), 1.66 (m, 2H), 1.45 (m, 5H), 1.26 (m, 3H), 0.82 (m, 1H), 0.52 (m, 2H), 0.12 (m, 2H).

$^{13}$C NMR (100 MHz, MeOH-d$_4$) δ 172.30, 149.20, 147.66, 146.05, 143.84, 142.16, 141.31, 132.55, 125.43, 122.40, 120.11, 118.63, 92.74, 71.79, 63.78, 60.27, 53.44, 45.34, 40.59, 35.16, 34.94, 31.83, 31.36, 27.84, 27.73, 27.05, 25.56, 23.59, 10.25, 4.48, 4.20.

IR (diamond, cm$^{-1}$) V$_{max}$ 3269.93, 2925.57, 2850.60, 1644.45, 1537.65, 1504.66, 1450.26, 1411.24, 1374.41, 1324.67, 1240.14, 1188.89, 1149.13, 1130.35, 1095.73, 1035.49, 984.59, 918.19, 881.92, 856.04, 828.64, 798.39, 785.52, 762.60, 745.35, 728.43, 702.73, 677.85.

Mass Spectrum C$_{32}$H$_{39}$N$_3$O$_4$ m/z calc. 529.2941 obs. 530.3025 [M+H]$^+$. Mp 248.6-249.7° C.

17-Cyclopropylmetyl-3,14β-dihydroxy-4,5α-epoxy-6β-[(3'-cyclohentanyl-4'-pyridyl) acetamido]morphinan (Compound 11)

Compound 11 was synthesized as shown in the general procedure with a yield of 65%.

$^1$H NMR (400 MHz, CDCl$_3$) δ 8.58 (s, 1H), 8.43 (m, 1H), 7.07 (m, 1H), 6.89 (m, 1H), 6.74 (d, J=8.1 Hz, 1H), 6.58 (d, J=8.1 Hz, 1H), 4.44 (d, J=7.8 Hz, 1H), 4.04 (m, 1H), 3.06 (m, 3H), 2.63 (m, 2H), 2.36 (m, 2H), 2.18 (m, 2H), 1.47-1.92 (m, 17H), 0.83 (m, 1H), 0.52 (m, 2H), 0.13 (m, 2H).

$^{13}$C NMR (100 MHz, MeOH-d$_4$) δ 170.34, 149.43, 147.35, 145.13, 143.83, 143.39, 142.18, 132.54, 125.41, 122.28, 120.11, 118.62, 92.74, 71.79, 63.78, 60.27, 53.43, 45.35, 42.38, 37.53, 37.42, 31.82, 31.36, 28.74, 28.73, 28.63, 28.47, 25.64, 23.59, 10.23, 4.48, 4.19.

IR (diamond, cm$^{-1}$) V$_{max}$ 3269.95, 3074.45, 2923.19, 2853.17, 1644.22, 1536.48, 1504.37, 1453.20, 1411.13, 1374.26, 1324.43, 1239.86, 1186.87, 1154.29, 1129.40, 1095.41, 1035.39, 984.37, 918.44, 896.79, 882.17, 856.61, 829.74, 798.64, 785.78, 762.42, 745.58, 728.45, 703.20, 676.77.

Mass Spectrum C$_{33}$H$_{41}$N$_3$O$_4$ m/z calc. 543.3097 obs. 544.3253 [M+H]$^+$. Mp 240.1-242.5° C.

17-Cyclopropylmetyl-3,14β-dihydroxy-4,5α-epoxy-6β-[(3'-Phenyl-4'-pyridyl) acetamido]morphinan (Compound 12)

Compound 12 was synthesized as shown in the general procedure with a yield of 60%

$^1$H NMR (400 MHz, DMSO-d$_6$) δ 9.06 (s, 1H), 8.66 (s, 1H), 8.65 (m, 2H), 7.48 (m, 4H), 7.37 (m, 2H), 6.60 (d, J=8.1 Hz, 1H), 6.51 (d, J=8.1 Hz, 1H), 4.43 (d, J=7.8 Hz, 1H), 3.48 (m, 1H), 3.17 (m, 1H), 2.96 (m, 2H), 2.56 (m, 2H), 2.30 (m, 2H), 2.07 (m, 1H), 1.96 (m, 1H), 1.82 (m, 1H), 1.54 (m, 1H), 1.39 (m, 1H), 1.23 (m, 3H), 0.83 (m, 1H), 0.46 (m, 2H), 0.11 (m, 2H).

$^{13}$C NMR (100 MHz, DMSO-d$_6$) δ 166.73, 150.11, 148.48, 143.55, 142.12, 140.48, 136.30, 133.45, 131.25, 128.25, 128.49, 127.80, 123.45, 121.48, 118.56, 117.07, 90.18, 69.51, 61.69, 58.33, 51.59, 48.57, 46.95, 43.67, 29.87, 23.71, 22.16, 9.18, 3.66, 3.49.

IR (diamond, cm$^{-1}$) V$_{max}$ 3267.19, 2926.62, 1759.45, 1655.72, 1537.27, 1490.98, 1477.79, 1445.55, 1399.94, 1329.53, 1277.45, 1236.21, 1200.83, 1154.28, 1131.52, 1095.64, 1068.52, 1037.44, 1006.16, 984.61, 934.19, 914.70, 880.93, 852.37, 793.70, 758.91, 699.07, 671.71.

Mass Spectrum C$_{32}$H$_{33}$N$_3$O$_4$ m/z calc. 523.2471 obs. 524.2552 [M+H]$^+$. Mp 232.4-235.2° C.

Biological Evaluation

Drugs and Chemicals.

Morphine (morphine sulfate pentahydrate salt) and naloxone, were procured from the National Institute of Drug Abuse (NIDA), Bethesda, Md. and then made into a 10 μM stock solution by dissolving in distilled water which was further diluted to the desired concentrations. All other reagents were purchased from either Sigma-Aldrich or Thermo Fisher.

Animals.

Male Swiss Webster mice (25-30 g, Harlan Laboratories, Indianapolis, Ind.) were raised in animal care quarters and maintained at room temperature on light-dark cycle. Food and water were available ad libitum. Protocols and procedures were approved by the Institutional Animal Care and Use Committee (IACUC) at Virginia Commonwealth University and complied with the recommendations of the IASP (International Association for the Study of Pain).

Competitive Radioligand Binding and [$^{35}$S]GTPγS Functional Studies.

In the competition binding assay, 30 μg of membrane protein was incubated with the corresponding radioligand in the presence of different concentrations of test compounds in TME buffer (50 mM Tris, 3 mM MgCl$_2$, and 0.2 mM EGTA, pH 7.4). The bound radioligand was separated by filtration using the Brandel harvester. Specific (i.e., opioid receptor-related) binding at the MOR, KOR, and DOR was determined as the difference in binding obtained in the absence and presence of 5 μM naltrexone, U50,488, and SNC80, respectively. The IC$_{50}$ values were determined and converted to K$_i$ values using the Cheng-Prusoff equation.

In the [$^{35}$S]GTPγS functional assay, 10 μg of MOR-CHO membrane protein was incubated with 10 μM GDP, 0.1 nM [$^{35}$S]GTPγS, assay buffer (TME+100 mM NaCl) and varying concentrations of the compounds under investigation for 90 minutes in a 30° C. water bath. Non-specific binding was determined with 20 μM unlabeled GTPγS. 3 μM of DAMGO was included in the assay as maximally effective concentration of a full agonist for the MOR. All assays were determined in duplicate and repeated at least 4 times. Percent DAMGO-stimulated [$^{35}$S]GTPγS binding was defined as (net-stimulated binding by ligand/net-stimulated binding by 3 μM DAMGO)×100%.

Data Analysis of [$^{35}$S]-GTPγS-Binding Assays.

All samples were assayed in duplicate and repeated at least four times for a total of ≥4 independent determinations. Results were reported as mean values±SEM. Concentration-effect curves were fit by nonlinear regression to a one-site binding model, using GraphPad Prism software, to determine EC$_{50}$ and Emax values. IC$_{50}$ values were obtained from Hill plots, analyzed by linear regression using GraphPad Prism software. Binding K$_i$ values were determined from IC$_{50}$ values using the Cheng-Prusoff equation: K$_i$=IC50/1+([L]/KD), where [L] is the concentration of competitor and K$_D$ is the K$_D$ of the radioligand.

Tail Immersion Test.

Swiss Webster mice were used for this experiment. Water bath temperature was maintained at 56±0.1° C. The baseline latency (control) was determined before the test compound was injected subcutaneously (s.c.) into the mice. The average baseline latency obtained for this experiment was 3.0±0.1 s and only mice with a baseline latency of 2 to 4 s were used. For the agonism study, tail immersion was conducted 20 min (time that morphine's antinociceptive effect starts to peak) after the test compound was injected. To prevent tissue damage, a 10 s maximum cut off time was imposed. Antinociception response was calculated as the percentage maximum possible effect (% MPE), where % MPE=[(test−control)/(10−control)]×100. For the antagonism study, the test compound was given 5 min before morphine. Tail immersion was conducted 20 min after giving morphine. % MPE was calculated for each mouse using at least five mice per drug. AD$_{50}$ values were calculated using the least-squares linear regression analysis followed by calculation of 95% confidence interval by Bliss method.

Withdrawal Assay.

Swiss Webster mice (male) were used for the withdrawal study. A 75 mg morphine pellet was implanted into the base of the neck of the mice and the mice were then given time to recover in their home cages. Before the test began, 30 min was given to the mice for habituation to an open-topped, square, clear Plexiglas observation chamber (26×26×26 cm$^3$) with lines partitioning the bottom into quadrants. All drugs and test compounds were administered by subcutaneous injection (s.c.). The withdrawal was precipitated 72 h from pellet implantation with naloxone (1 mg/kg, s.c.), and the test compounds at different doses. Withdrawal commenced within 3 min after antagonist administration. Escape jumps, paw tremors, and wet dog shakes were quantified by counting their occurrences over 20 min for each mouse (five mice per group). The data is shown as the mean±SEM.

Statistical Analysis.

One-way ANOVA followed by the posthoc Dunnett test were performed to assess significance using Prism 6.0 software (GraphPad Software, San Diego, Calif.).

Docking Study

The crystal structures of the MOR (PDB ID: 4DKL), KOR (PDB ID: 4DJH) and DOR (PDB ID: 4EJ4) obtained from the Protein Data Bank at http://www.rcsb.org. Sybyl-X 2.0 was used to add hydrogen atoms to each receptor and to sketch NFP (TRIPOS Inc., St. Louis, Mo.). NFP was then assigned Gasteiger-Hückel charges and energy minimized to a gradient of 0.05 under the TAFF in Sybyl-X 2.0.

GOLD 5.4 with default settings was used to conduct the docking study. The atoms within 10 Å of the γ-carbon atom of D$^{3.32}$ of the MOR, KOR, and DOR were defined as the binding site in the three receptors. Automated docking was conducted with a distance constraint of 4 Å between the nitrogen atom at the 17' position of the epoxymorphinan nucleus and the conserved D$^{3.32}$. In addition, a hydrogen bond constraint was applied between NFP's dihydrofuran oxygen and the phenolic oxygen of the conserved Y$^{3.33}$. The highest scored solutions (CHEM-PLP) were selected and merged into the receptor to obtain the optimal binding poses of NFP in the MOR, KOR, and DOR. After docking, the binding poses were energy minimized in Sybyl-X 2.0.7 with 5000 iterations under TAFF to remove the clashes and strain energy between NFP and the three receptors.

Example 2. Pharmacological Characterization of 17-cyclopropylmethyl-3,14-dihydroxy-4,5-epoxy-6-[(3'-fluoro-4'-pyridyl)acetamido]morphinan (NFP) as a Dual Selective MOR/KOR Ligand Abbreviations for Example 2

G-protein coupled receptors (GPCRs), μ opioid receptor (MOR), К opioid receptor (KOR), δ opioid receptor (DOR), Food and Drug Administration (FDA), Chinese hamster ovary cell lines expressing mouse monocloned α opioid receptor (mMOR-CHO), Hank's balanced salt solution (HBSS), Dulbecco's modified Eagle's medium (DMEM), fetal bovine serum (FBS), Phosphate buffered saline (PBS), paraformaldehyde (PFA), transepithelial electrical resistance (TEER), P-glycoprotein (P-gp), permeability directional ratio (PDR), basolateral-to-apical permeability ($P_{app,\ B-A}$), apical-to-basolateral permeability ($P_{app,\ A-B}$), percent maximum possible effect (% MPE), Chinese hamster ovary (CHO). 17-cyclopropylmethyl-3,14β-dihydroxy-4,5α-epoxy-6β-(4'-pyridylcarboxamido)morphinan (NAP), 17-cyclopropylmethyl-3,14-dihydroxy-4,5-epoxy-6-[(3'-fluoro-4'-pyridyl)acetamido]morphinan (NFP).
2. Materials and Methods
2.1 Calcium Mobilization Assay A Chinese hamster ovary cell line stably expressing the mouse μ opioid receptor (mMOR-CHO) was used for this assay. The cells were transfected with $G_{\alpha qi5}$ for 4 hours and then plated (3,000,000 cells/well) to black 96-well plates with clear bottoms (Greiner Bio-One). After 24 hours of incubation, the culture media was removed and the cells were washed with assay buffer (50 mL HBSS, 1 mL HEPES, 250 μL probenecid, 50 μL 1 mM $CaCl_2$, 50 μL 1 mM $MgCl_2$).

For agonist assays, cells were then incubated with 50 μL/well loading buffer (6 mL assay buffer, 24 μL Fluo4-AM solution (Invitrogen), 12 μL probenecid solution) for 45 min. Following incubation, different concentrations of the test compounds were added by FLEXSTATION®3 microplate reader (Molecular Devices) and read at ex494/em516. Each concentration was run in triplicate.

For antagonism studies, the cells were incubated with the same loading buffer as the agonist assay for 45 min. Then, different concentrations of the test compounds (20 μL/well) were manually added to each well followed by another 15 min incubation. After that, the solution of DAMGO in assay buffer (500 nM) or just assay buffer (blank) was added by FLEXSTATION®3 microplate reader (Molecular Devices) and read at ex 494/em 516. Each concentration was run in triplicate.

The corresponding $EC_{50}$ or $IC_{50}$ value of each compound was calculated by GraphPad Prism 6.0 (GraphPad Software, San Diego, Calif.).
2.2 Downregulation and Desensitization Study
2.2.1 Incubation of mMOR-CHO Cells with Opioid Ligands mMOR-CHO cells were grown in culture media (DMEM/F12 media, 10% FBS, 1% penicillin/streptomycin, 0.5% G418) for 5 days in an incubator set at 37° C. with 5% $CO_2$ and 95% humidity. On the fifth day when the cells were confluent, the culture media was removed and the cells were rinsed with 5 mL PBS. The cells were then treated with DAMGO (5 μM), morphine (5 μM), nalbuphine (1 μM), NFP (1 μM), naltrexone (1 μM) and vehicle (0.02% DMSO) dissolved in DMEM/F12 media and incubated for 24 h. After incubation, the treatment media was removed and the cells were washed three times with 10 mL phosphate-buffered saline (PBS). 5 mL PBS was added to each dish and the cells were then scraped off the dishes using a scraper. The cells were then centrifuged at 1,000×g for 10 min. After centrifugation, the supernatant was decanted and membrane buffer (50 mM Tris, 3 mM $MgCl_2$, and 1 mM EGTA, pH 7.4) was added to each sample. The cells were then homogenized and centrifuged again at 50,000×g for 10 min. The supernatant was decanted and the cells were homogenized again in membrane buffer. A Bradford assay was conducted to determine the concentration of the membrane protein. The membrane protein preparations were then stored at −80° C.
2.2.2 mMOR Receptor Saturation Assay Membranes were homogenized in membrane buffer and centrifuged at 50,000×g for 10 min. This step was repeated to ensure that the drugs were completely removed from the receptor. The supernatant was then decanted and membranes were re-suspended in 50 mM Tris, 3 mM $MgCl_2$, and 0.2 mM EGTA (pH 7.4). A Bradford assay was conducted to determine the protein concentration. The MOR membrane protein (30 μg) was then incubated with varying concentrations of [$^3$H]naloxone (specific activity=66.58 Ci/mmol) for 90 min at 30° C. Nonspecific binding was determined using 5 μM naltrexone. The incubation was terminated by rapid filtration and bound radioactivity was determined as described previously (Selley et al., 1998). $K_D$ and $B_{max}$ values were determined by non-linear regression using GraphPad Prism 6.0 (GraphPad Software, San Diego, Calif.).
2.2.3 [$^{35}$S]GTP γS Binding Assay Ligand-stimulated [$^{35}$S]GTPγS binding was performed as described previously (Selley et al., 1998). Briefly, membranes from the treated mMOR-CHO cells (10 μg of protein) were incubated with 0.1 nM [$^{35}$S]GTPγS (specific radioactivity was 1250 Ci/mmol) and 20 μM GDP for 90 min at 30° C. with varying concentrations of DAMGO in assay buffer (50 mM Tris-HCl, 3 mM $MgCl_2$, 100 mM NaCl, 0.2 mM EGTA, pH 7.4). Nonspecific binding was determined with 20 μM unlabeled GTPγS and basal binding was determined in the absence of MOR ligand. The incubation was terminated by rapid filtration through GF/B glass fiber filters and rinsed three times with ice-cold wash buffer (50 mM Tris-HCl, pH 7.2). Bound radioactivity was determined by liquid scintillation spectrophotometry at 95% efficiency for $^{35}$S. Net-stimulated [$^{35}$S]GTPγS binding was defined as ligand-stimulated minus basal binding.
2.3 MOR Internalization
2.3.1 Cell Culture Neuro2 Å murine neuroblastoma cells (N2A cells) stably transfected with the rat MOR cDNA epitope-tagged with HA at N-terminus (N2A-HA-rMOR) were established previously (Obeng, et al., 2019) and clones H38 and H16 expressing MOR at 1-2 pmole/mg protein were used in the study. Cells were cultured in 10-cm dishes at 37° C. with 5% $CO_2$ in humidified air in MEM (Minimum Essential Medium, ref 41500, Gibco, NY) supplemented with 10% FBS and penicillin, streptomycin and amphotericin (A5955, Sigma, MO) and grew to 80% confluence.
2.3.2 MOR Internalization MOR internalization experiments were conducted as described previously (Obeng, et al., 2019) Briefly, N2A-HA-rMOR cells were sub-cultured onto coverslips placed in 6-well plates at 300,000 cells per well. Forty-eight hours later, mouse anti-HA. 11 antibodies (Clone 16B 12, BioLegend, CA) were added at 1:1000 to cell medium and incubated for 1 h. NFP (final 10 μM) or vehicle was added and incubated for 15 min followed by addition of etorphine (final 10 µM) or vehicle and incubated for another 15 min. Cells were cooled on ice, washed, and fixed with 4% paraformaldehyde (PFA) in PB for 15 min, and washed. Cells were then incubated with ALEXA FLUOR®594 goat anti-mouse IgG (1:1000) (A11005, Invitrogen, OR) on a shaker with light protection for 2 h at room temperature. After washing, the cells on cover slips were mounted on slides using mounting medium (H-1200, Vector Laboratories, CA) and cured overnight. The images were acquired by a Nikon Eclipse TE300 fluoresce microscope coupled to a digital camera (MagnaFire) using 20× objective and processed with ImageJ.

2.4 Caco-2 Bidirectional Transport Assay 2.4.1 Transport of NFP in Caco-2 Cell Line Caco-2 cells (passage 48; ATCC, Manassas, Va.) were plated on 12 mm, 0.4 m, #3460-Clear TRANSWELL® inserts (Corning Incorporated, Corning, N.Y.) at an initial seeding density of 90,000 cells/well. The cells were cultured in DMEM supplemented with 10% FBS and non-essential amino acids for 23 days. On day 24, the medium was removed and the transwells were rinsed with PBS. HBSS buffer (pH 7.4) was added to both apical (0.5 mL) and basolateral (1.5 mL) chambers and the initial transepithelial electrical resistance (TEER) values were recorded. The blank HBSS buffer in apical or basolateral chambers was replaced by NFP solutions in HBSS (20 µM) with or without P-glycoprotein (P-gp) inhibitor (elacridar, 1 µM) (Matsson et al., 2009). 200 µL aliquots were collected from the receiver chamber up to 2 h. Acetonitrile (50 µL) was added to each sample (50 µL), which was vortexed then centrifuged at 10,000 g for 5 min at 20° C. The supernatant was then used for analysis by LC-MS as described below. At the end of 2 h, the solution in both chambers was replaced with HBSS and post-experiment TEER values were measured. The integrity of the monolayers was confirmed by studying the transport of lucifer yellow, a low permeability marker (Maharao et al. 2017) The permeability directional ratio (PDR) was calculated as the ratio of basolateral-to-apical permeability to apical-to-basolateral permeability ($P_{app, B-A}/P_{app, A-B}$).

2.4.2 LC-MS Conditions

Chromatographic separation was achieved using a Waters HPLC system (Waters Corporation, Milford, Mass.). The analyte NFP was separated on a Thermo Scientific HYPERSIL™ BDS C18 column (50×4.6 mm, 3 am; Waltham, Mass.) with isocratic elution (aq. 0.1% formic acid and acetonitrile, 85:15). The flow rate was 1.0 mL/min and the temperature of the column was maintained at 35° C. The injection volume was 40 µL. The MS system consisted of an ACQUITY® QDA® mass spectrometer (Waters Corporation, Milford, Mass.) equipped with electrospray ionization in the positive ion detection mode. The run time for each sample was 5.20 min. Data acquisition and processing were performed using Empower 3 software (Waters Corporation, Milford, Mass., USA). The retention time for NFP was found to be 2.99 min and had an m/z value of 466.20 ([NFP+H]$^+$).

2.5 Warm-Water Tail-Withdrawal Test

Adult male C57BL/6J mice (Jackson Laboratory, Bar Harbor, Me.) were individually housed in a temperature-controlled (20-22° C.) AAALAC-accredited facility in which they had ad libitum access to food and water. The mice were maintained on a 12 h/12 h light-dark cycle (0600-1800 lights on) for the duration of the experiment and were tested during the light segment of this cycle. All subjects were acclimated to the vivarium for at least one week before the commencement of studies.

Apparatus and Drugs:

A commercial warm water bath (Model #JBN5 US; Grant Instruments Ltd., Cambridge, UK) maintained at 52.5±0.5° C. was used to assess nociception. Tail withdrawal latencies were measured with a digital stopwatch (Model #14-649-7; Fisher Scientific, Pittsburgh, Pa.). Morphine sulfate was obtained from the NIDA Drug Supply Program. All compounds were dissolved in sterile saline (Fisher Scientific, Pittsburgh, Pa.; Cat. #125EZ-7002) and were administered s.c. All compounds were administered in a volume equivalent to 10 mL/kg body weight. Technicians were blinded to treatment groups.

Warm-Water Tail-Withdrawal Tests:

Mice were randomly assigned to either the Vehicle Group or the 0.3 mg/kg NFP Group (N=6/group). Each group was tested twice; once on Day 1 prior to chronic dosing with morphine, and once on Day 7 following chronic dosing.

Day 1 Tests:

At the start of testing of Day 1, each mouse was placed in a restraint cloth fashioned from a surgical drape, and the distal 3 cm of its tail was submerged in the warm water bath to determine its baseline withdrawal latency. A digital stopwatch was used to record the amount of time that elapsed between tail immersion and tail withdrawal (i.e., tail-withdrawal latency). Immediately after that, mice received consecutive injections of saline (i.e., morphine's vehicle) and their scheduled NFP condition (i.e., vehicle or 0.3 mg/kg NFP), and were returned to their home cage. After a 30-min pretreatment period had elapsed, tail-withdrawal latencies were re-determined, and mice were immediately injected with the lowest dose of morphine (1 mg/kg). Following the 30-min pretreatment period, tail-withdrawal latencies were re-determined, and the next highest dose of morphine was administered (i.e., acutely 2.2 mg/kg resulting in a cumulative dose of 3.2 mg/kg). This process was repeated with cumulative doses of 10 and 32 mg/kg morphine. A 10-s cutoff time was imposed across all assessments to minimize potential tissue damage.

Days 2-6:

On non-test days (i.e., Days 2-6) at a similar time each afternoon (between 1400 and 1500 hours), mice received two injections one right after the other, either 10 mg/kg morphine+NFP vehicle (Vehicle Group) or 10 mg/kg morphine+0.3 mg/kg NFP (NFP Group).

Day 7 Tests:

Approximately 24 h after receiving the last set of injections on Day 6, mice were re-assessed in the warm-water tail-withdrawal procedure with cumulative morphine dosese identical to that described for Day 1.

Data Analysis:

Tail-withdrawal latencies were recorded for each animal and data were expressed as percent maximum possible effect (% MPE) as follows: [(test-baseline)/(10−baseline)*100]. Within group analyses were conducted separately for % MPE data generated during Day 1 and Day 7 for each group using a repeated measure ANOVA with morphine dose as the within-subjects factor. Fisher's LSD post-hoc tests were used to identify significant differences of morphine dose vs baseline. Separate two-way ANOVAs comparing % MPE scores between the Vehicle and NFP groups during Day 1 and Day 7 were additionally conducted. Data were subsequently analyzed using Fisher's LSD post-hoc tests comparing Vehicle and NFP groups at each morphine dose on each day. All statistical tests were conducted using microcomputer software (Prism 7 for Mac OSX, GraphPad Software, Inc., San Diego, Calif.), and all types of comparisons were considered statistically significant if p<0.05.

3. Results 3.1 Calcium Mobilization Assay

[$^{35}$S]-GTPγS binding assays directly measure the activation of G-proteins induced by a ligand binding to its receptor, whereas calcium mobilization assays measure the release of calcium as a readout of more downstream intracellular signaling cascade (Selly et al., 1998). After stimulated by a ligand, the conformation of the GPCR changes, thus activating its corresponding intracellular downstream messenger pathway. As a result of these variations, cytosolic calcium is released which can be measured using a fluorescent calcium indicator (Zhu et al., 2008). Chinese hamster ovary (CHO) cell lines expressing the μ opioid receptor were used for this assay. DAMGO and naltrexone were used as control compounds. The assay was carried out as described previously (Yuan et al., 2013). As seen in FIG. 7A, the full MOR agonist DAMGO displayed a concentration-dependent relationship in enhancing Ca$^{2+}$ signal (EC$_{50}$=36.32±1.85 nM). However, NFP did not induce any apparent Ca$^{2+}$ signal as compared with DAMGO, even at the highest concentration (3 μM) indicating a lack of agonist properties. For the antagonism assay (FIG. 7B), both NFP and naltrexone inhibited DAMGO (500 nM)-induced calcium flux in a concentration-dependent manner, which confirmed the antagonist properties of NFP and naltrexone. Compared to naltrexone (IC$_{50}$=6.62±1.45 nM), NFP inhibited the DAMGO stimulated calcium flux with a lower potency (IC$_{50}$=76.09±2.5 nM).

3.2 Downregulation and Desensitization Study

To validate the potential application of NFP in opioid addiction treatments, it is important to study its capacity to desensitize and/or downregulate opioid receptors. Here, DAMGO (opioid agonist), morphine (opioid agonist), nalbuphine (opioid partial agonist), and naltrexone (opioid antagonist) were used as control compounds. CHO cell lines expressing the μ opioid receptor (mMOR-CHO) were pretreated with vehicle or ligand, washed and DAMGO-induced [$^{35}$S]GTPγS binding was performed.

As shown in Table 5, compared with the vehicle treated group, the DAMGO EC$_{50}$ values of the cells treated with morphine and DAMGO increased about 6- and 4-fold, respectively, this indicates that morphine and DAMGO desensitized the MOR. Conversely, the DAMGO EC$_{50}$ values of nalbuphine, naltrexone and NFP treated cells were similar to the DAMGO EC$_{50}$ value for the vehicle treated cells (Table 5). These results demonstrated that cells pretreated with opioid agonists morphine or DAMGO desensitized MOR mediated G-protein activation compared with the vehicle pretreated cells. However, the cells pretreated with opioid partial agonists (nalbuphine and NFP) or the opioid antagonist (naltrexone) did not desensitize the activation of G-proteins mediated by the MOR. This conclusion was further confirmed by the efficiency of receptors determined as E$_{max}$/EC$_{50}$ (Table 5). These results showed that cells pretreated with morphine and DAMGO significantly reduced the efficiency of the MOR, while the cells pretreated with nalbuphine, naltrexone, and NFP did not show noticeable desensitization compared to the vehicle group.

TABLE 5

B$_{max}$, K$_D$ values and EC$_{50}$ and E$_{max}$ values of [$^3$H] naloxone saturation binding and GTPγS functional assay, respectively in opioid ligand-pretreated MOR-CHO cell membranes.

| Pretreatment | B$_{max}$ (pmol/mg) | K$_D$ (nM) | EC$_{50}$ (nM) | E$_{max}$ (net fmol/mg) | Efficiency (E$_{max}$/EC$_{50}$) |
|---|---|---|---|---|---|
| Vehicle† | 2.90 ± 0.24 | 1.16 ± 0.23 | 27.54 ± 3.78 | 123.04 ± 11.93 | 4.47 |
| DAMGO† | 1.49 ± 0.12* | 1.96 ± 0.07 | 120.83 ± 6.97* | 121.62 ± 13.78 | 1.01 |
| Morphine† | 1.58 ± 0.10* | 1.84 ± 0.28 | 168.43 ± 6.25* | 140.63 ± 6.59 | 0.83 |
| NFP | 2.10 ± 0.15 | 3.22 ± 0.32* | 53.95 ± 9.87 | 156.20 ± 13.83 | 2.90 |
| Nalbuphine† | 3.66 ± 0.26 | 1.70 ± 0.10 | 48.40 ± 5.65 | 165.63 ± 6.52 | 3.42 |
| Naltrexone† | 3.86 ± 0.68 | 3.84 ± 0.44* | 21.85 ± 0.78 | 126.73 ± 3.97 | 5.80 |

Data are mean ± SEM of B$_{max}$, KD, EC$_{50}$ and E$_{max}$ values derived from non-linear regression analysis of [$^3$H]naloxone saturation binding and mMOR-stimulated [$^{35}$S]GTPγS binding curves (n = 4).
*p <0.05, different from corresponding value in vehicle-pretreated cells.
†Values previously published (Obeng et al., 2018, 2019).

As described previously, desensitization may induce downregulation in the number of opioid receptors. Therefore, it is important to discern whether the compound induces MOR downregulation due to desensitization. To address this concern, a mMOR-CHO saturation binding assay using [$^3$H]-naloxone was applied to determine K$_D$ and B$_{max}$ values (Kostenis et al., 2005; Allouche et al., 2008; Christie et al., 2008). As the results demonstrated (Table 1), compared with vehicle pretreated group, there was significant MOR downregulation seen in cells pretreated with morphine and DAMGO, whereas nalbuphine, naltrexone and NFP did not induce significant downregulation of the MOR. Cells pretreated with naltrexone and NFP had almost three times greater K$_D$ values compared to the vehicle group, which was not seen in cells pretreated with morphine, DAMGO and nalbuphine. These results showed that cells pretreated with opioid agonists morphine or DAMGO, not only decreased DAMGO's potency at the MOR but also reduced receptor efficiency (E$_{max}$/EC$_{50}$). In addition, the opioid agonists produced downregulation of the MOR. Both of these facts may contribute to opioid tolerance. Interestingly, NFP did not show significant desensitization and downregulation of the MOR. This suggests NFP has the potential to be used therapeutically for opioid use disorder treatments without likely producing tolerance.

3.3 MOR Internalization

Desensitization and downregulation of opioid receptors may occur following prolonged binding of opioid agonists to the receptors, e.g. due to internalization via different mechanisms.

Following internalization, receptors may be recycled or downregulated. NFP did not cause significant desensitization and downregulation of the MOR. We examined if NFP promoted MOR internalization. Two different N2A-HA-rMOR-N2A cell lines were used for this assay because CHO cells have a small cytosolic volume and it is difficult to visualize receptor internalization. The opioid agonist etorphine was used as a positive control. Duplicate experiments showed that etorphine (10 μM) distinctly induced internalization of the MOR, whereas NFP (10 μM) did not (data not shown). Interestingly, when etorphine and NFP were incubated together (10 μM respectively), internalization of the MOR induced by etorphine was reduced. These results indicated that NFP can antagonize the MOR internalization induced by etorphine and were consistent with those of the downregulation and desensitization studies.

3.4 Caco-2 Bidirectional Transport Assay

As described in Example 1, NFP showed evident MOR antagonism in in vivo studies with an $AD_{50}$ value of 2.82 (1.34-5.94) mg/kg with a 95% confidence level (CL). Additionally, NFP precipitated dramatically fewer withdrawal symptoms compared with naloxone at the same doses. These characteristics were maintained even at the highest dose (100 mg/kg) tested. However, the potency of NFP was lower than that of naloxone ($AD_{50}$=0.05 mg/kg). To address this discrepancy, a bidirectional transport (apical-to-basolateral and basolateral-to-apical) assay was conducted to simulate and assess the bidirectional permeability of NFP in the human gastrointestinal tract and test whether NFP is a P-gp substrate.

Figure 8:
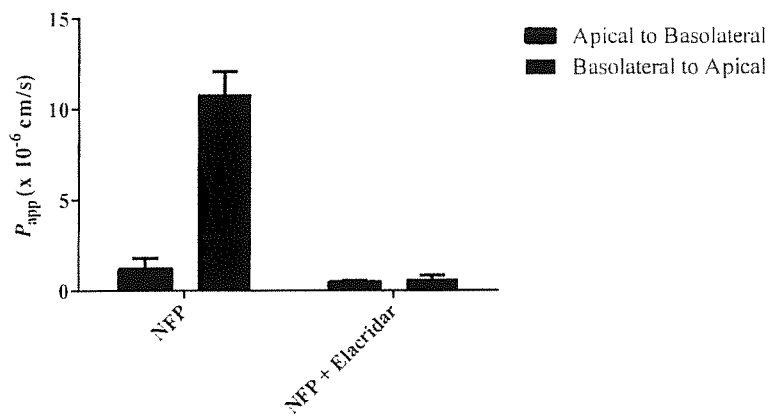
FIG. 8. The result of bidirectional transport assay for NFP. $P_{app}$ values of tested compounds in apical-to-basolatoral (A-B) and basolateral-to-apical (B-A) directions were determined by incubating Caco-2 monolayers at 37° C. for 2 h with NFP (20 μM). Data represent means±SD.

The net TEER values for the transwells greater than 200 $\Omega \cdot cm^2$, and a $P_{app}$ of $<1 \times 10^6$ cm/s for lucifer yellow confirmed the integrity of the Caco-2 monolayers (Maharao et al., 2017). As seen in FIG. 8, the basolateral-to-apical permeability ($P_{app, B-A}$, efflux) of NFP (20 μM) is much higher than the apical-to-basolateral permeability ($P_{app, A-B}$, absorption). However, when the P-gp inhibitor elacridar (10 μM) was added, it reduced the B-A transport significantly more than A-B transport. Elacridar reduced the PDR value of NFP from 7.0±0.5 to 1.3±0.3, consistent with P-gp transport activity. A similar phenomenon is also seen with a well-known P-gp substrate, digoxin. In a related study, the PDR of digoxin decreased from 5.1 to 1.2 after elacridar was added. These results suggest that NFP may be a P-gp substrate.

3.5 Warm-Water Tail-Withdrawal Assay

As described previously, NFP was shown to act as a CNS partial agonist (Example 1) without apparent desensitization and downregulation effects. Moreover, it did not precipitate significant withdrawal symptoms as compared with naloxone, even at high doses. To further evaluate its CNS pharmacological profile, a warm-water tail-withdrawal test was used in a morphine cumulative-dosing mouse model.

Figures 9A, 9B:
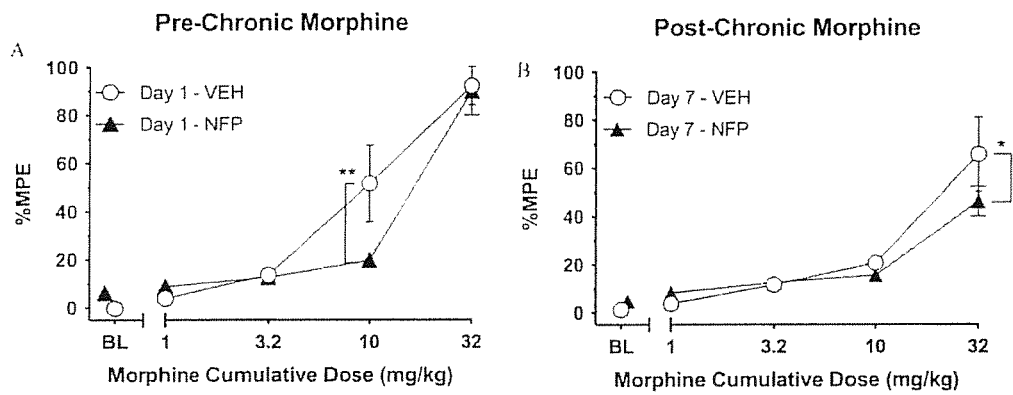
FIGS. 9A and B. The result of the warm-water tail-withdrawal test. (A) Effects of vehicle ("VEH", i.e., saline) or NFP (0.3 mg/kg, s.c.) pretreatment on warm-water tail-withdrawal latencies following cumulative doses of morphine (1-32 mg/kg, s.c.) expressed as percent maximum possible effect (% MPE). Values represent the mean (±SEM) percent maximum possible effect (% MPE) of 6 mice. Unfilled circles represent % MPE values following saline pretreatment. Filled triangles represent results following pretreatment with 0.3 mg/kg NFP. ** indicates NFP pretreatment resulted in a lower % MPE score than the vehicle treated group; p=0.0013. (B) Results of cumulative doses of morphine on warm-water tail-withdrawal latencies in the Vehicle and NFP Groups following five days of dosing with 10 mg/kg morphine+either saline or 0.3 mg/kg NFP. * indicates NFP pretreatment resulted in a lower % MPE score than the vehicle treated group; p=0.0138

Day 1 results of morphine cumulative dosing tests for both groups are presented in FIG. 9A. These results indicated that morphine produced significant increases in % MPE relative to baseline conditions at doses of 10 (p<0.0001) and 32 (p<0.0001) mg/kg in the vehicle-pretreated group, and of 32 (p<0.0001) mg/kg in the NFP-pretreated group. However, 10 mg/kg morphine produced significantly less antinociception in the NFP group relative to the vehicle-treated group (p=0.0013) demonstrating that NFP reduces the antinociceptive effects of morphine at 10 mg/kg. However, this antagonism was surmounted by increasing the dose to 32 mg/kg morphine.

After seven days, there were significant main effects of morphine dose (p<0.0001) and a significant interaction (p<0.0420). Results (FIG. 9B) indicated that morphine only produced a significant increase in % MPE relative to baseline conditions at a dose of 32 mg/kg for both the vehicle-pretreated (p<0.0001) and NFP-pretreated (p<0.0001) groups. Morphine produced significantly less antinociception in the NFP group relative to the Vehicle Group at the dose of 32 mg/kg (p=0.0138).

4. Discussion and Conclusion

The pharmacological profile of NFP was further evaluated to determine its applications in opioid tolerance and opioid use disorder treatment. NFP displayed opioid antagonism in the calcium flux assay. Additionally, in desensitization studies, it was shown that NFP did not produce desensitization and downregulation of the MOR. In fact, NFP showed the ability to antagonize internalization of the MOR following desensitization by opioid agonists. Though NFP may be a P-gp substrate in vitro, in vivo studies demonstrated its ability to block morphine's antinociceptive effects in a 7 day warm-water tail-withdrawal assay. Overall, these studies indicate that NFP is suitable for use as a therapeutic candidate for the treatment of opioid use disorder, without producing tolerance or inducing withdrawal symptoms.

Example 3

Scheme 3. Synthesis of NAP derivatives (Compounds 13-17).[1]

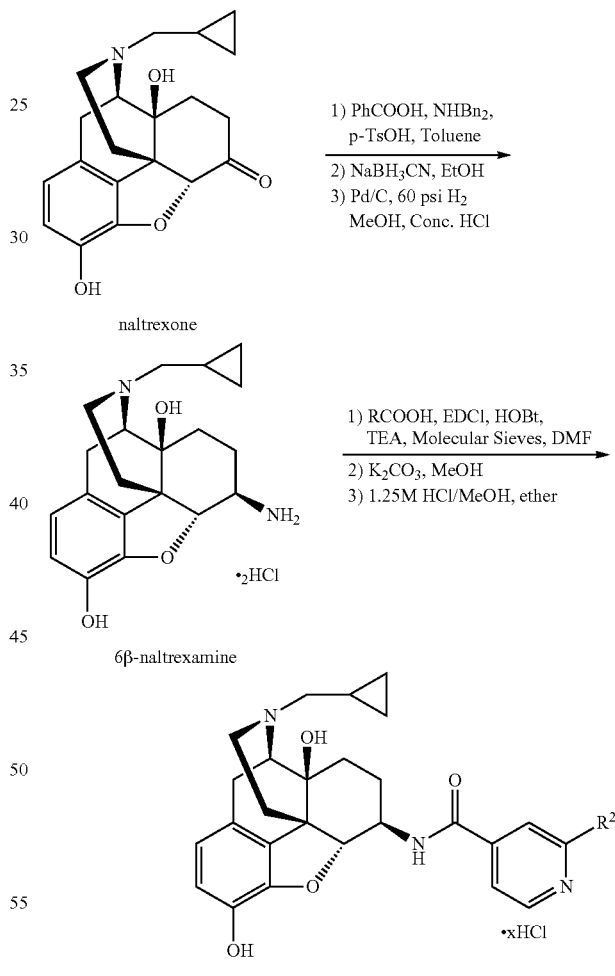

Chemistry

Chemical reagents were purchased from either Sigma-Aldrich or Alfa Aesar. TLC analyses were carried out on Analtech Uniplate F254 plates. Chromatographic purification was accomplished on silica gel columns (230-400 mesh, Merck). Melting points were obtained with a Fisher Scientific micro melting point apparatus without correction. IR spectra were recorded on either a Nicolet iS10 or a Nicolet Avatar 360 FT-IR Instrument. Proton (400 MHz) and carbon-13 (100 MHz) nuclear magnetic resonance (NMR) spectra were acquired at ambient temperature with tetramethylsilane as the internal standard on a Bruker Ultrashield 400 Plus spectrometer. MS analysis was performed on an Applied Bio Systems 3200 Q trap with a turbo V source for TurbolonSpray. HPLC analysis was done with a Varian ProStar 210 system on Microsorb-MV 100-5 C8/C18 column (250 mm×4.6 mm) at 254 nm, eluting with acetonitrile (0.1% TFA)/water (50/50 or 35/65) at 1 mL/min over 30 min. Elemental analysis was conducted in Atlantic Microlab, Inc. Specific rotation was gained on the JASCO DIP-1000 digital polarimeter and given as the mean value of three measurements. All above analytical methods were used to determine purity of the newly synthesized compounds, and their purity is confirmed as ≥95%.

Synthesis of 6β-Naltrexamine Hydrochloride Salt

6β-naltrexamine hydrochloride salt was synthesized as previously reported.[2]

General Procedure for Synthesis of Target Compounds (13-17)

On an ice-water bath, to a solution of acid (3 equiv) in anhydrous DMF (3 mL) was added N-(3-dimethylaminopropyl)-N'-ethylcarbodiimide hydrochloride (EDCI, 3 equiv), hydrobenzotriazole (HOBt, 3 equiv), 4 Å molecular sieves, and TEA (5.0 equiv) with $N_2$ protection. Fifteen minutes later, a solution of 6β-naltroxamine hydrochloride (1.0 equiv) in DMF (1 mL) was added dropwise. The resulting mixture was allowed to warm to ambient temperature gradually. Upon completion of the reaction, the mixture was then filtered through Celite. The filtrate was concentrated to remove DMF. Methanol (5 mL) and $K_2CO_3$ (2 equiv) were then added to the residue and stirred at ambient temperature overnight. The mixture was then filtered through Celite again. The filtrate was concentrated to remove methanol. The residue was partitioned between $CH_2Cl_2$ (50 mL) and brine (50 mL). The organic layer was separated, dried over anhydrous $MgSO_4$, and concentrated under reduced pressure. The residue was then purified by column chromatography, eluting with $CH_2Cl_2$/MeOH (1% $NH_3$—$H_2O$) to afford the corresponding compound as free base. Upon confirmation by $^1H$ NMR and $^{13}C$ NMR, the free base was then transformed into hydrochloride salt by dissolving in MeOH (0.1 mL) and DCM (2 mL), adding HCl methanol solution (1.25 M, 4 equiv) with an ice-water bath, and stirring for 5 min. Diethyl ether (10 mL) was then added. Two hours later, the precipitate was collected by filtration and dried in vacuum to give the target compound as a hydrochloride salt, which was used in HPLC, MS, specific rotation, and elemental analysis.

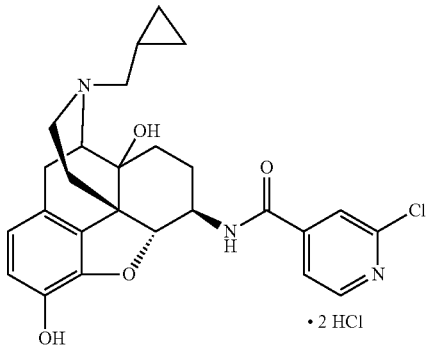

17-Cyclopropylmethyl-3,14β-dihydroxy-4,5α-epoxy-6β-{[4'-(2'-chloropyridyl)]carboxamido}morphinan (13)

The title compound was obtained following the general procedure as a yellow solid, in 88% yield. $[\alpha]^{25}_D$ –105.64° (c 1.0, MeOH). Free base: $^1H$ NMR (300 MHz, $CDCl_3$) δ 8.43 (d, J=5.1 Hz, 1H), 8.08 (d, J=8.7 Hz, 1H), 7.73 (m, 1H), 7.62 (dd, J=5.4, 1.5 Hz, 1H), 6.61 (d, J=8.1 Hz, 1H), 6.54 (d, J=8.1 Hz, 1H), 4.71 (d, J=6.0 Hz, 1H), 3.98 (m, 1H), 3.16 (d, J=5.7 Hz, 1H), 3.03 (d, J=18.6 Hz, 1H), 2.65 (m, 2H), 2.38 (d, J=6.6 Hz, 2H), 2.19 (m, 2H), 2.02 (m, 1H), 1.67 (m, 2H), 1.49 (m, 2H), 0.85 (m, 1H), 0.55 (m, 2H), 0.13 (m, 2H); $^{13}C$ NMR (75 MHz, $CDCl_3$) δ 200.8, 164.1, 154.6, 152.5, 150.6, 144.6, 139.5, 130.7, 124.9, 122.5, 120.3, 117.9, 92.3, 70.6, 62.4, 59.6, 51.5, 47.6, 44.1, 35.3, 31.9, 29.5, 23.5, 9.6, 4.3, 4.1. MS m/z found 482.6 (M+H)$^+$. IR (KBr, cm$^{-1}$) $v_{max}$ 3250.3, 1660.3, 1550.4, 1498.7, 1317.8, 1136.8. Mp>250° C. Anal. ($C_{26}H_{28}ClN_3O_4$·2HCl·1.5$H_2O$) C, H, N.

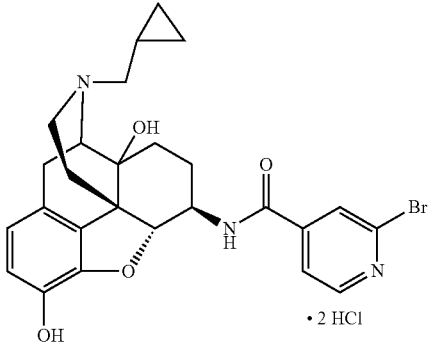

17-Cyclopropylmethyl-3,14β-dihydroxy-4,5α-epoxy-6β-{[4'-(2'-bromopyridyl)]carboxamido}morphinan (14)

The title compound was obtained following the general procedure as a light yellow solid, in 62% yield. $[\alpha]^{25}_D$ –141.75° (c 1.0, MeOH). Free base: $^1H$ NMR (300 MHz, $CDCl_3$) δ 8.41 (d, J=5.1 Hz, 1H), 8.19 (d, J=8.7 Hz, 1H), 7.91 (m, 1H), 7.68 (dd, J=5.4, 1.5 Hz, 1H), 6.60 (d, J=8.4 Hz, 1H), 6.55 (d, J=8.1 Hz, 1H), 4.80 (d, J=6.6 Hz, 1H), 3.91 (m, 1H), 3.19 (d, J=5.4 Hz, 1H), 3.05 (d, J=18.3 Hz, 1H), 2.68 (m, 2H), 2.39 (m, 2H), 2.19 (m, 3H), 1.70 (m, 2H), 1.46

(m, 2H), 0.85 (m, 1H), 0.55 (m, 2H), 0.15 (m, 2H); $^1$H NMR (300 MHz, CD$_3$OD) δ 8.54 (d, J=4.8 Hz, 1H), 8.04 (d, J=1.2 Hz, 1H), 7.81 (dd, J=5.4, 1.5 Hz, 1H), 6.71 (m, 2H), 4.71 (d, J=7.8 Hz, 1H), 3.90 (m, 1H), 3.43 (m, 1H), 3.24 (m, 1H), 2.85 (m, 3H), 2.62 (m, 1H), 2.40 (m, 2H), 2.02 (m, 1H), 1.77-1.53 (m, 4H), 1.02 (m, 1H), 0.67 (m, 2H), 0.32 (m, 2H); $^{13}$C NMR (75 MHz, CD$_3$OD) δ 204.7, 166.2, 152.1, 146.4, 143.7, 143.6, 142.4, 132.1, 127.4, 122.2, 120.6, 119.0, 92.5, 71.8, 64.0, 59.9, 53.8, 48.7, 46.4, 31.4, 31.1, 25.3, 23.9, 9.4, 5.2, 4.1. MS m/z found 526.1 (M+H)$^+$. IR (KBr, cm$^{-1}$) $v_{max}$ 3398.9, 1673.2, 1544.0, 1498.7, 1472.9, 1324.4, 1130.3. Mp>250° C. Anal.

(C$_{26}$H$_{28}$BrN$_3$O$_4$·2HCl·1.5H$_2$O) C, H, N.

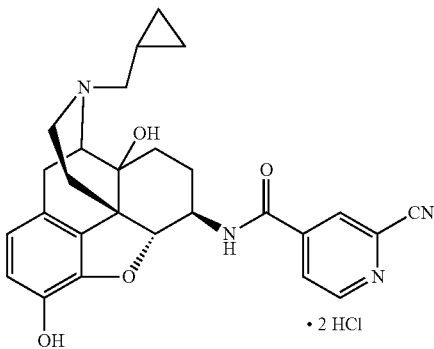

17-Cyclopropylmethyl-3,14β-dihydroxy-4,5α-epoxy-6β-{[4'-(2'-cyanopyridyl)]carboxamido}morphinan (15)

The title compound was obtained following the general procedure as a light yellow solid, in 48% yield. [α]$^{25}$$_D$–146.12° (c 0.5, MeOH).

Hydrochloride salt: $^1$H NMR (400 MHz, DMSO-d$_6$) δ 9.15 (s, 1H), 8.76 (m, 1H), 8.68 (brs, 1H), 8.25 (dd, J=0.64, 1.44 Hz, 1H), 7.95 (dd, J=1.62, 5.06 Hz, 1H), 6.55 (d, J=8.16 Hz, 1H), 6.49 (d, J=8.16 Hz, 1H), 6.02 (s, 1H), 4.62 (d, J=7.76 Hz, 1H), 3.69 (d, J=5.16 Hz, 1H), 3.54-3.48 (m, 1H), 3.19 (m, 2H), 2.94-2.85 (m, 2H), 2.68 (m, 1H), 2.27 (m, 1H), 2.26 (m, 1H), 1.78-1.69 (m, 1H), 1.60 (m, 1H), 1.43 (m, 1H), 1.34-1.21 (m, 2H), 0.89 (m, 1H), 0.50 (m, 1H), 0.42 (m, 1H), 0.35 (m, 1H), 0.24 (m, 1H); $^{13}$C NMR (100 MHz, DMSO-d$_6$) δ 162.16, 152.15, 142.42, 142.00, 141.34, 133.25, 129.51, 126.43, 125.28, 120.60, 119.41, 117.96, 117.19, 89.54, 69.63, 61.65, 56.69, 51.64, 46.46, 45.60, 29.27, 27.30, 23.45, 23.01, 5.70, 5.10, 2.62. MS m/z found 473.6 (M+H)$^+$. IR (diamond, cm$^{-1}$) $V_{max}$ 3084.0, 2234.1, 1655.9, 1536.6, 1503.1, 1323.1, 1128.0, 1031.0, 919.8, 857.9, 747.8. Mp 251° C., dec.

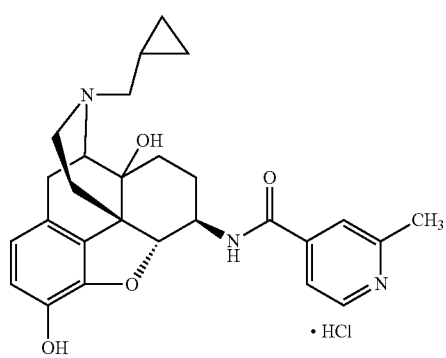

17-Cyclopropylmethyl-3,14β-dihydroxy-4,5α-epoxy-6β-{[4'-(2'-methylpyridyl)]carboxamido}morphinan (16)

The title compound was obtained following the general procedure as a light yellow solid, in 66% yield. [t]$^{25}$$_D$–202.18° (c 1.0, MeOH). Free base: $^1$H NMR (400 MHz, CDCl$_3$) δ 8.58 (d, J=5.2 Hz, 1H), 7.49 (s, 1H), 7.39 (d, J=8.8 Hz, 1H), 7.31 (d, J=5.2 Hz, 1H), 6.73 (d, J=8.0 Hz, 1H), 6.57 (d, J=8.4 Hz, 1H), 4.49 (d, J=6.0 Hz, 1H), 4.12 (m, 1H), 3.13 (d, J=6.0 Hz, 1H), 3.04 (d, J=18.4 Hz, 1H), 2.65 (m, 2H), 2.60 (s, 3H), 2.38 (d, J=4.8 Hz, 2H), 2.21 (d, J=7.6 Hz, 2H), 1.81 (m, 1H), 1.67 (m, 1H), 1.58 (m, 1H), 1.53 (m, 2H), 0.86 (m, 1H), 0.54 (d, J=8.0 Hz, 2H), 0.14 (d, J=4.8 Hz, 2H); $^{13}$C NMR (100 MHz, CDCl$_3$) δ 164.88, 158.92, 148.87, 143.11, 141.90, 140.04, 130.53, 123.97, 121.26, 119.11, 118.27, 118.01, 91.47, 70.23, 62.13, 59.15, 51.06, 47.23, 43.87, 31.39, 29.21, 23.67, 23.41, 22.53, 9.30, 3.94, 3.66. Hydrochloride salt: $^1$H NMR (400 MHz, DMSO-d$_6$) δ 9.34 (brs, 1H, exchangeable), 9.01 (d, J=7.2 Hz, 1H, exchangeable), 8.88 (brs, 1H, exchangeable), 8.64 (d, J=4.8 Hz, 1H), 7.76 (s, 1H), 7.66 (d, J=4.8 Hz, 1H), 6.73 (d, J=8.4 Hz, 1H, Ar—H), 6.66 (d, J=8.0 Hz, 1H, Ar—H), 6.23 (brs, 1H), 4.82 (d, J=8.0 Hz, 1H), 3.89 (m, 1H), 3.69 (m, 1H), 3.36 (m, 2H), 3.06 (m, 2H), 2.85 (m, 1H), 2.57 (s, 3H), 2.45 (m, 2H), 1.90 (m, 1H), 1.78 (m, 1H), 1.59 (m, 1H), 1.44 (m, 2H), 1.07 (m, 1H), 0.67 (m, 1H), 0.59 (m, 1H), 0.50 (m, 1H), 0.42 (m, 1H); $^{13}$C NMR (100 MHz, DMSO-d$_6$) δ 163.92, 158.14, 148.51, 142.23, 142.04, 141.34, 129.60, 121.23, 120.60, 119.30, 118.81, 117.90, 89.62, 69.66, 61.53, 56.64, 51.37, 46.46, 45.58, 29.29, 27.28, 23.59, 23.43, 23.02, 5.73, 5.13, 2.62. MS m/z found 462.4 (M+H)$^+$. IR (diamond, cm$^{-1}$) $v_{max}$ 3181.9, 3057.7, 2936.5, 1661.1, 1609.4, 1543.5, 1505.1, 1452.0, 1346.1, 1273.8, 1240.9, 1125.0, 1032.3. Mp 248° C., dec. Anal. (C$_{27}$H$_{31}$N$_3$O$_4$·HCl·2H$_2$O) C, H, N.

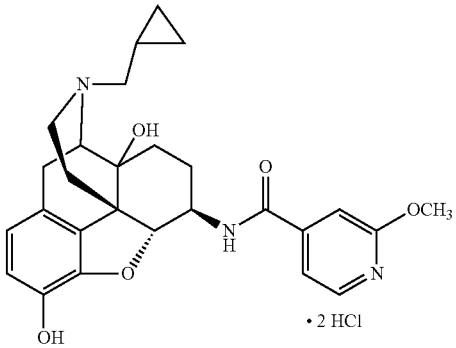

17-Cyclopropylmethyl-3,14β-dihydroxy-4,5α-epoxy-6β-{[4'-(2'-methoxypyridyl)]carboxamido}morphinan (17)

The title compound was prepared by following the general procedure, in 62% yield. [α]$^{25}$$_D$–179.44° (c 0.8, MeOH). Hydrochloride salt: $^1$H NMR (400 MHz, DMSO-d$_6$) δ 8.94 (d, J=8.04 Hz, 1H), 8.88 (brs, 1H), 8.31 (d, J=5.24 Hz, 1H), 7.40 (dd, J=5.2, 1.2 Hz, 1H), 7.25 (m, 1H), 6.73 (d, J=8.0 Hz, 1H), 6.65 (d, J=8.4 Hz, 1H), 4.83 (d, J=8.0 Hz, 1H), 3.90 (m, 4H), 3.67 (m, 1H), 3.34 (m, 2H), 3.05 (m, 2H), 2.86 (m, 1H), 2.45 (m, 2H), 1.90 (m, 1H), 1.78 (m, 1H), 1.58 (m, 1H), 1.43 (m, 2H), 1.08 (m, 1H), 0.67 (m, 1H), 0.59 (m, 1H), 0.52 (m, 1H), 0.41 (m, 1H); $^{13}$C NMR (100 MHz, DMSO-$d_6$) δ 164.10, 163.63, 147.53, 144.34, 141.98, 141.24, 129.49, 120.52, 119.26, 117.86, 114.55, 108.25, 89.51, 69.60, 61.59, 56.61, 53.51, 51.27, 46.39, 45.51, 29.23, 27.23, 23.47, 22.94, 5.63, 5.02, 2.54. MS m/z found 478.2 (M+H)$^+$. IR (diamond, cm$^{-1}$) $v_{max}$ 3390.5, 3172.6, 3116.7, 1659.7, 1617.9, 1547.9, 1422.0, 1372.2, 1329.2, 1276.0, 1131.8, 1033.6, 919.4, 859.7, 811.6.

Mp 244-248° C., dec. Anal. ($C_{27}H_{31}N_3O_5$·2HCl·2.5H$_2$O) C, H, N.

References for Example 3

1. Yuan, Y.; Elbegdorj, O.; Chen, J.; Akubathini, S K.; Zhang, F.; Stevens, D. L.; Beletskaya, I. O.; Scoggins, K. L.; Zhang, Z.; Gerk, P. M.; Selley, D. E.; Akbarali, H. I.; Dewey, W. L.; Zhang, Y. Design, synthesis, and biological evaluation of 17-cyclopropylmethyl-3,14β-dihydroxy-4,5α-epoxy-6β-[(4'-pyridyl)carboxamido]morphinan derivatives as peripheral selective μ opioid receptor Agents. *J. Med. Chem.* 2012, 55, 10118-10129.

2. Sayre, L. M.; Portoghese, P. S. Stereospecific synthesis of the 6.alpha.- and 6.beta.-amino derivatives of naltrexone and oxymorphone. *J. Org. Chem.* 1980, 45, 3366-3368.

While the invention has been described in terms of its preferred embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

I claim:

1. A compound of Formula Ia:

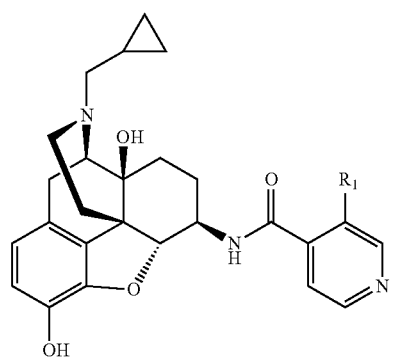

Formula Ia wherein, $R_1$ is F, NO$_2$, CF$_3$, COOH, COOCH$_3$, C$_2$H$_5$, isobutyl, cyclopentyl, cyclohexyl, cycloheptyl or phenyl.

2. A compound of Formula Ib

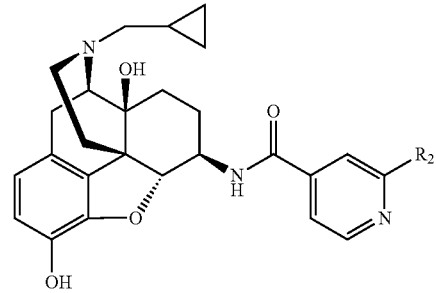

Formula Ib wherein $R_2$ is Cl, Br, CN, or CH$_3$.

3. A method of treating opioid use disorders, alcoholism, pain, and/or a neurological disorder associated with opioid receptors in a subject in need thereof, comprising administering to the subject a therapeutically effective amount of i) a compound of Formula Ia:

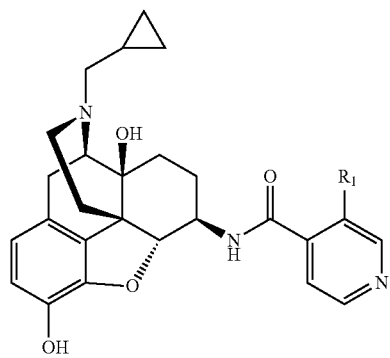

Formula Ia wherein $R_1$ is F, CN, NO$_2$, CF$_3$, COOH, COOCH$_3$, C$_2$H$_5$, isobutyl, cyclopentyl, cyclohexyl, cycloheptyl or phenyl;

or ii) a compound of Formula Ib:

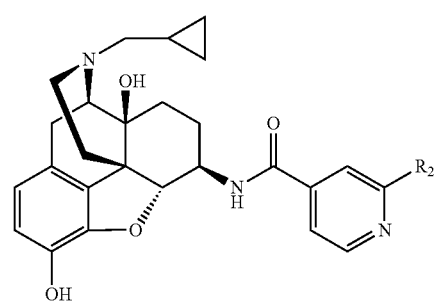

Formula Ib wherein $R_2$ is Cl, Br, CN, CH$_3$ or OCH$_3$.

4. A method of modulating a μ opioid receptor (MOR), comprising
contacting the MOR with
i) a compound of Formula Ia:

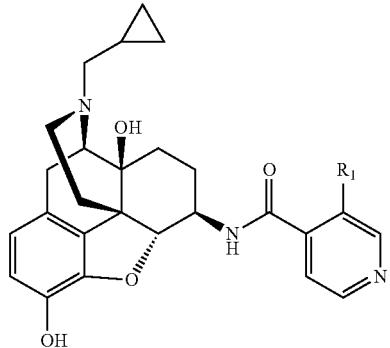

Formula Ia wherein $R_1$ is F, CN, $NO_2$, $CF_3$, COOH, $COOCH_3$, $C_2H_5$, isobutyl, cyclopentyl, cyclohexyl, cycloheptyl or phenyl;

or ii) a compound of Formula Ib:

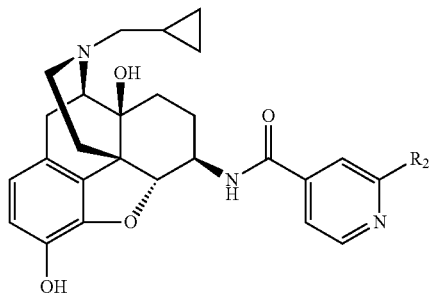

Formula Ib wherein R2 is Cl, Br, CN, $CH_3$ or $OCH_3$;

wherein the step of contacting is performed under conditions that permit binding of the compound to the MOR and modulating the MOR.

5. The method of claim 4, wherein the step of contacting is performed in vivo in a subject or in vitro in a cultured cell.

6. The method of claim 5, wherein the cultured cell overexpresses the MOR.

* * * * *